(12) United States Patent
Schwab et al.

(10) Patent No.: US 12,325,019 B1
(45) Date of Patent: Jun. 10, 2025

(54) LIQUID HOLDING ASSEMBLY

(71) Applicant: UrynX, LLC, East Chatham, NY (US)

(72) Inventors: Brian Schwab, East Chatham, NY (US); Michael Fabrizio, East Chatham, NY (US); Matthew Neururer, East Chatham, NY (US)

(73) Assignee: UrynX, LLC, East Chatham, NY (US)

(*) Notice: Subject to any disclaimer, the term of this patent is extended or adjusted under 35 U.S.C. 154(b) by 0 days.

(21) Appl. No.: 17/665,485

(22) Filed: Feb. 4, 2022

(51) Int. Cl.
*B01L 3/00* (2006.01)
*A61B 10/00* (2006.01)
*G01N 33/543* (2006.01)

(52) U.S. Cl.
CPC .......... *B01L 3/5023* (2013.01); *A61B 10/007* (2013.01); *G01N 33/54387* (2021.08); *B01L 2300/043* (2013.01); *B01L 2300/069* (2013.01); *B01L 2400/0481* (2013.01)

(58) Field of Classification Search
None
See application file for complete search history.

(56) References Cited

U.S. PATENT DOCUMENTS

| 5,268,148 | A | * | 12/1993 | Seymour | A61B 10/0051 422/547 |
| 8,871,155 | B2 | * | 10/2014 | Wu | B01L 3/5023 422/402 |
| 10,980,520 | B2 | * | 4/2021 | Green | A61B 10/007 |
| 11,090,648 | B2 | * | 8/2021 | Fuller | G01N 33/487 |
| 2007/0128070 | A1 | * | 6/2007 | Wu | A61B 10/0051 422/400 |

* cited by examiner

Primary Examiner — Lore R Jarrett
(74) Attorney, Agent, or Firm — Michael D. Eisenberg

(57) ABSTRACT

A liquid holding assembly, comprising a first tube and a second tube. The first tube has a first longitudinal wall extending between a closed first bottom end and a first top end. The second tube is configured to be inserted in the first tube, and a second longitudinal wall extending between a closed second bottom end and a second top end, the second bottom end having a perforation and comprising a holding unit configured to hold a sponge below the second bottom end. The second tube is configured to be inserted into the first tube to compress the sponge between the first bottom end and the second bottom end, to cause the sponge to release a liquid absorbed therein. A tight fit between the first longitudinal wall and the second bottom end is configured to force the released liquid to travel into the second tube via the perforation.

18 Claims, 31 Drawing Sheets

LIQUID HOLDING ASSEMBLY

BACKGROUND OF THE INVENTION

The spread of pandemics (COVID-19) and migration patterns where people are increasingly moving to exurban locations are factors which impose difficulties in obtaining biological samples or specimens for diagnostic testing. The contagiousness of COVID-19 has necessitated people to isolate from others. Diagnostic testing is needed which can use facilely obtained biological samples, while minimizing the risk of spreading pandemics (i.e., increasing safety when obtaining biological samples or specimens and efficiency for diagnostic testing). Exurban locations often lack the facilities for rapid, efficient, and safe diagnostic testing.

SUMMARY OF THE EMBODIMENTS OF THE INVENTION

In view of the above, an aim of the present invention is to enhance the efficiency of rapid and safe diagnostic testing for isolated populations.

Therefore, an aspect of some embodiments of the present invention relates to a liquid holding assembly, comprising a first tube and a second tube. The first tube has a closed first bottom end, an open first top end, and a first longitudinal wall extending between the first bottom end and the first top end, the first longitudinal wall enclosing an inner cavity of the first tube and having a first inner surface facing the inner cavity and a first outer surface facing outward from the first tube. The second tube is configured to be inserted in the first tube, and has a closed second bottom end, a second top end, and a second longitudinal wall extending between the second bottom end and the second top end, the second bottom end having a perforation and comprising a holding unit configured to hold a sponge below the second bottom end, and the second bottom end being configured to fit tightly against the first longitudinal wall when inserted into the first tube. The sponge is configured to absorb a liquid. The second tube is configured to be inserted into the first tube to compress the sponge between the first bottom end and the second bottom end. The sponge is configured to release the liquid when compressed. A tight fit between the first longitudinal wall and the second bottom end is configured to prevent passage of the liquid released by the sponge into the first tube above the second bottom end of the second tube, such that the liquid released by the sponge is forced to travel into the second tube via the perforation in the second bottom end.

In a variant, the second tube is configured to hold a test strip, and the liquid released by the sponge when the sponge is compressed between the first bottom end the second bottom end is forced to travel into the second tube via the perforation in the second bottom end and to contact the test strip in the second tube.

In another variant, the second top end is configured to extend above the first top end when the second tube is fully inserted into the first tube.

In some embodiments of the present invention, the liquid holding assembly comprises a cap covering the second top end of the second tube.

The cap may be configured to be removably joined to the second tube.

In a variant, an upper section of the second longitudinal wall comprises first threads, the cap comprises second threads configured to cooperate with the first threads, and the cap is configured to be joined to the second tube by screwing the cap onto the top section of the second longitudinal wall.

In another variant, the second tube is configured to hold a test strip, and the liquid released by the sponge when the sponge is compressed between the first bottom end the second bottom end is forced to travel into the second tube via the perforation in the second bottom end and to contact the test strip in the second tube. The cap comprises a cover, a duct, and a lid. The cover covers the second top end and having a second perforation. The duct extends around and above the second perforation. The lid is hinged to the cover, the lid being configured to selectively snap onto and away from the cover to close and open the duct. The second tube is configured to contain the test strip such that a bottom portion of the test strip is inside the second tube and configured to contact the liquid released by the sponge, while a top portion of the test strip extends out of the second perforation in the duct.

In some embodiments of the present invention the second tube comprises an upper reservoir and a channel. The upper reservoir is located below the second top end. The channel is located between the upper reservoir and above the second bottom end, the channel being in fluid communication the upper reservoir and with the perforation at the second bottom end. The channel is radially narrower than the upper reservoir and the second bottom end.

In a variant, the second tube is configured to hold a test strip, the liquid released by the sponge when the sponge is compressed between the first bottom end the second bottom end is forced to travel into the second tube via the perforation in the second bottom end and to contact the test strip in the second tube, and the channel is sized to contain a portion of the test strip and to keep the portion of the test strip substantially parallel to a central axis of the second tube.

In another variant, the liquid holding assembly comprises at least two panels extending radially from an outer surface of the channel between the upper reservoir and second bottom end.

In a variant, the first tube comprises a platform below the first bottom end, the platform widening as the platform extends away from the first bottom end.

In another variant, the second bottom end comprises a flat platform having a non-zero longitudinal height, and the second bottom end is radially surrounded by a sealing ring to enhance the tight fit between the first longitudinal wall and the second bottom end.

In yet another variant, the liquid holding assembly comprises the test strip.

In a further variant, the liquid holding assembly comprises the sponge.

In yet a further variant, the liquid is urine.

In a variant, the liquid is urine, and the test strip comprises one or more reagent pads configured to react with the urine according to characteristics of the urine, such that a reaction results in a color change of the reagent pad.

Another aspect of some embodiments of the present invention relate to a liquid holding assembly, comprising a first, tube, a sponge, a test strip, and second tube. The first tube has a closed first bottom end, an open first top end, and a first longitudinal wall extending between the first bottom end and the first top end, the first longitudinal wall enclosing an inner cavity of the first tube, the first longitudinal wall having an inner surface and an outer surface, the inner surface facing the inner cavity and the outer surface facing outward from the first tube. The sponge is configured to absorb a liquid. The test strip is configured to react with the liquid upon contact with the liquid. The second tube is configured to contain the test strip and to be inserted in the first tube, the second tube having a closed second bottom end, a second top end, and a second longitudinal wall extending between the second bottom end and the second top end and surrounding the test strip, the second bottom end having a perforation, the second bottom end comprising a holding unit configured to hold the sponge below the second bottom end, and the second bottom end being configured to fit tightly against the first longitudinal wall when inserted into the first tube. The second tube is configured to be inserted into the first tube to compress the sponge between the first bottom end and the second bottom end. The sponge is configured to release the liquid when compressed. A tight fit between the first longitudinal wall and the second bottom end is configured to prevent passage of the liquid released by the sponge into the first tube above the second bottom end of the second tube, such that the liquid released by the sponge is forced to travel into the second tube via the perforation in the second bottom end and to contact the test strip in the second tube.

In a variant, the liquid holding assembly includes a cap covering the second top end of the second tube, the cap comprising a cover, a duct, and a lid. The cover covers the second top end of the second tube having a second perforation. The duct extends around perforation and upward from the cover. The lid is hinged to the cover, the lid being configured to selectively snap onto and away from the cover to close and open the duct. The test strip is contained in the second tube such that a bottom portion of the test strip is inside the test strip and configured to contact the liquid released by the sponge, while a top end of the test strip extends out of the second perforation in the duct.

The cap may be removably joined to the second tube.

In another variant, the liquid is urine and the test strip comprises one or more reagent pads configured to react with the urine according to characteristics of the urine, such that a reaction results in a color change of the reagent pad.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

FIG. 13 is a perspective view of the threaded second tube of FIG. 12a;

DETAILED DESCRIPTION OF THE EMBODIMENTS OF THE INVENTION

From time-to-time, the present invention is described herein in terms of example environments. Description in terms of these environments is provided to allow the various features and embodiments of the invention to be portrayed in the context of an exemplary application. After reading this description, it will become apparent to one of ordinary skill in the art how the invention can be implemented in different and alternative environments.

Reference is also made to the figures, as presented herein. The figures are not intended to be exhaustive or to limit the invention to the precise form disclosed. It should be understood that the invention can be practiced with modification and alteration, and that the invention be limited only by the claims and the equivalents thereof.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in applications, published applications and other publications that are herein incorporated by reference, the definition set forth in this document prevails over the definition that is incorporated herein by reference.

Figure 1:
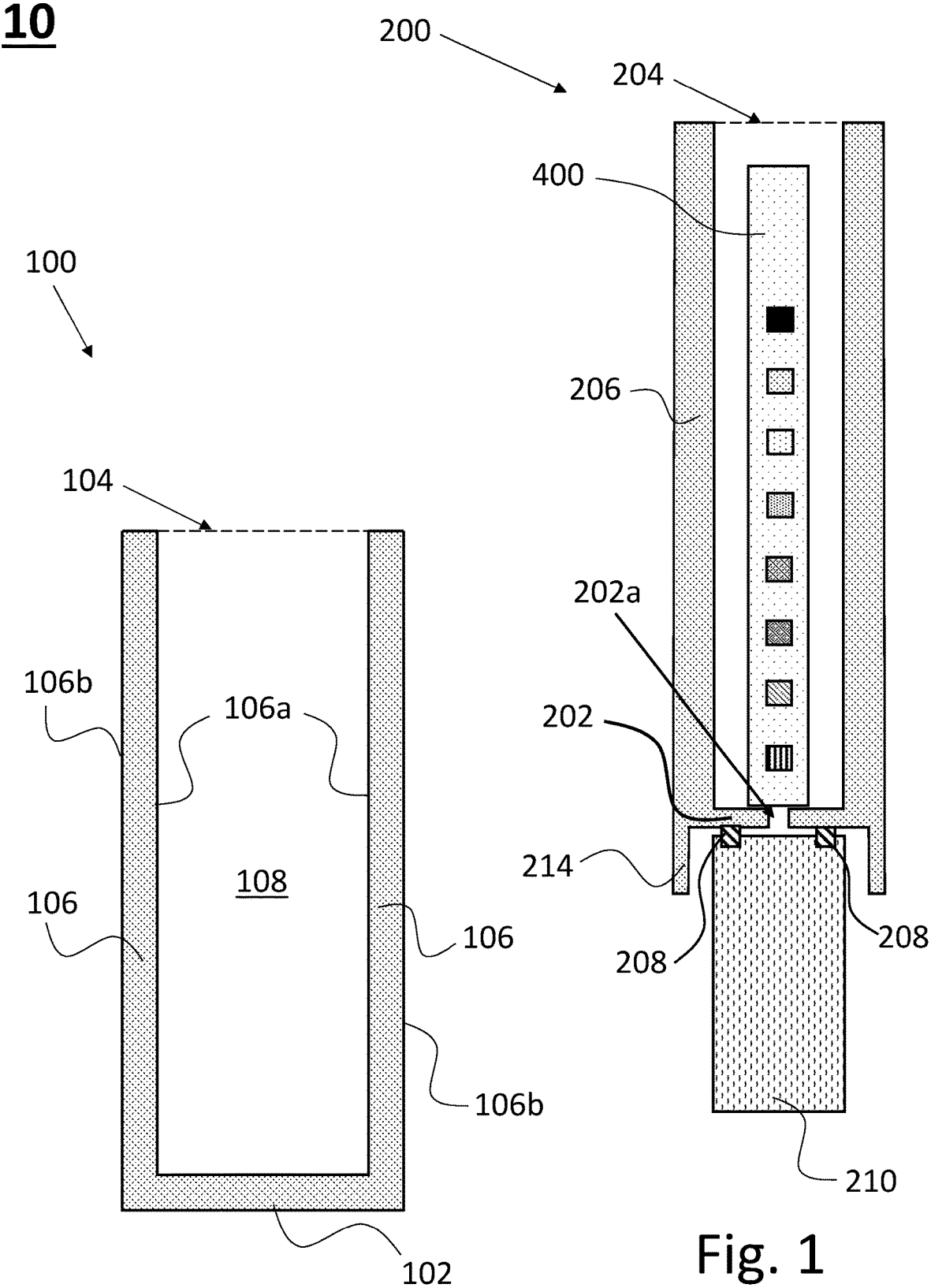
FIG. 1 is a side cross-sectional view of a liquid holding assembly of the present invention, in which a first tube and a second tube are detached from each other.
Figure 2:
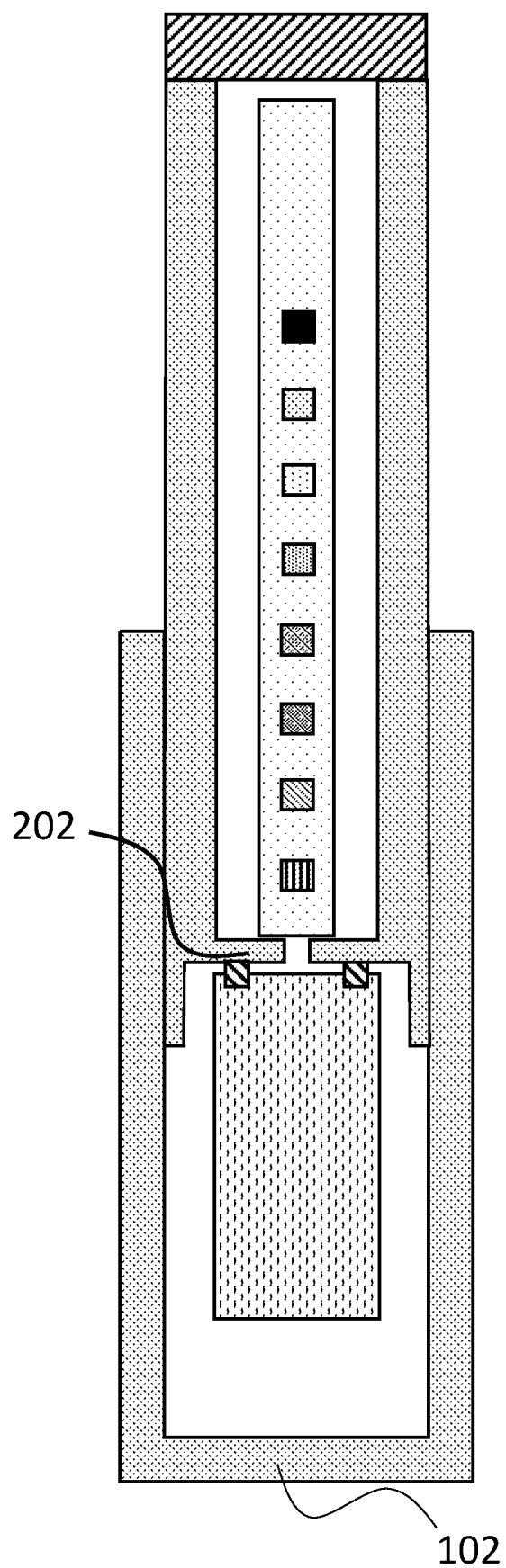
FIGS. 2-4 are side cross-section views of the liquid holding assembly of FIG. 1, in which the second tube is inserted into the first tube, such that a sponge held by the second tube is compressed between the first tube and the second tube and releases a liquid absorbed within the sponge into the second tube.
Figure 3:
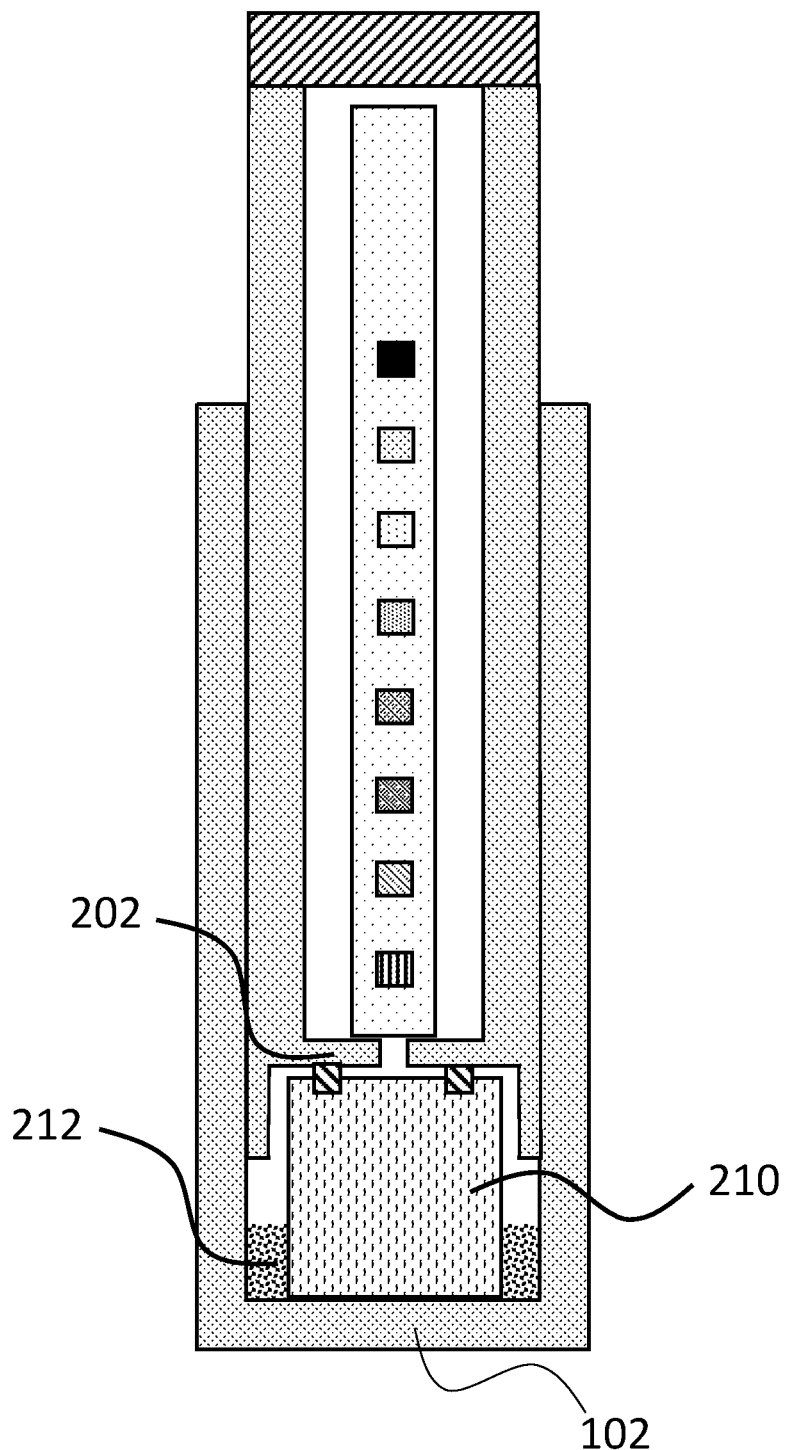
Figure 4:
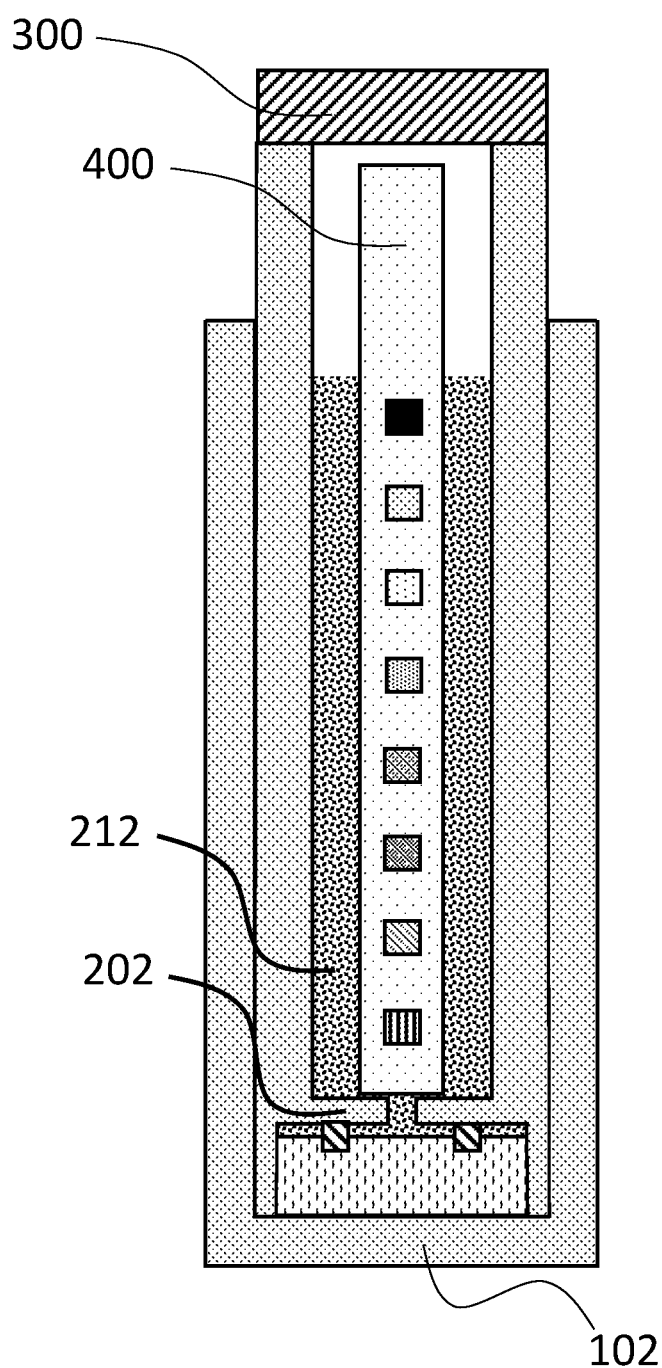
Figure 5:
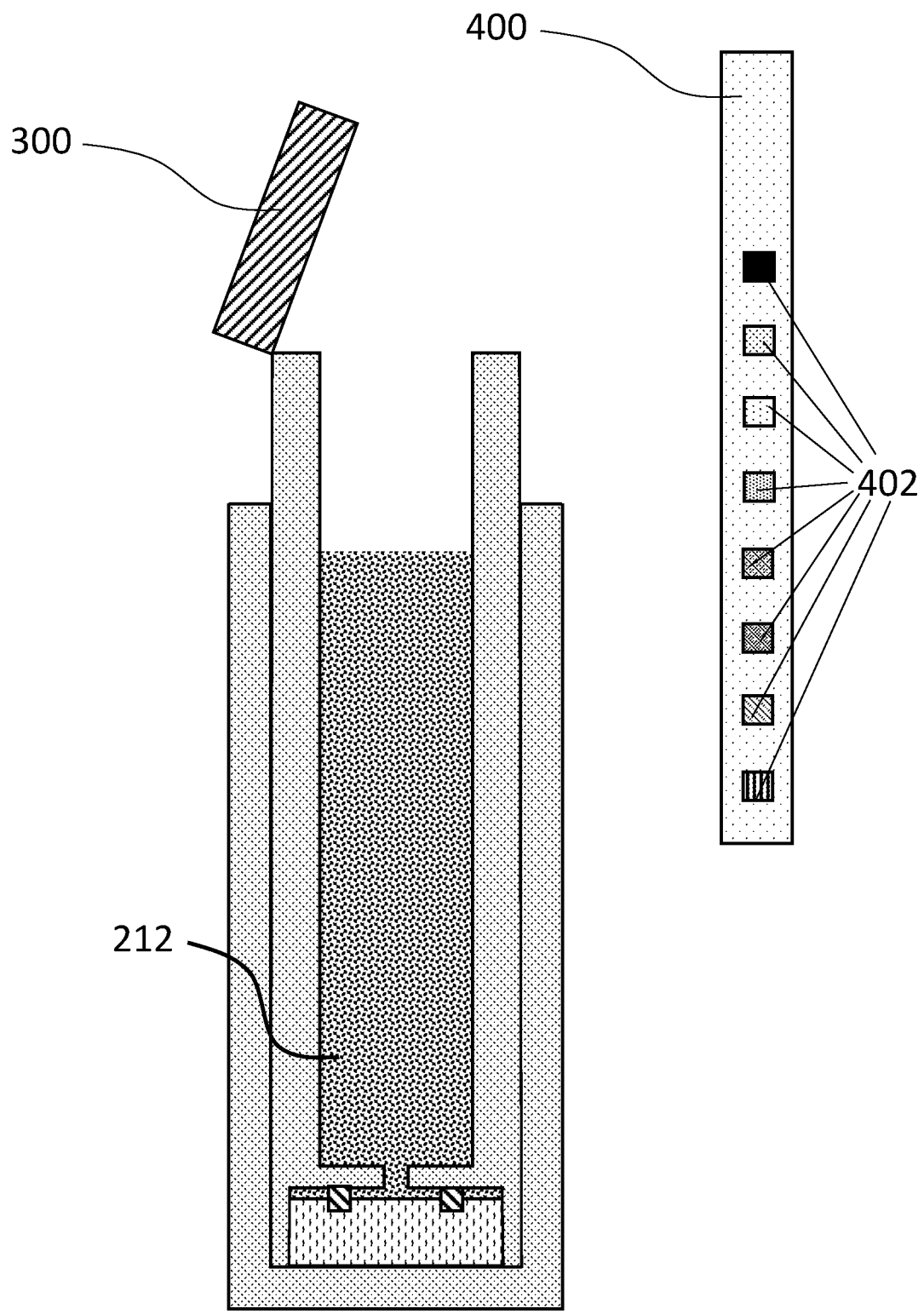
FIG. 5 is a side cross-sectional view of the liquid holding assembly of FIGS. 1-4, in which a test strip is removed from the second tube via a cap, after the test strip has contacted the liquid, in some embodiments of the present invention.
Figure 6:
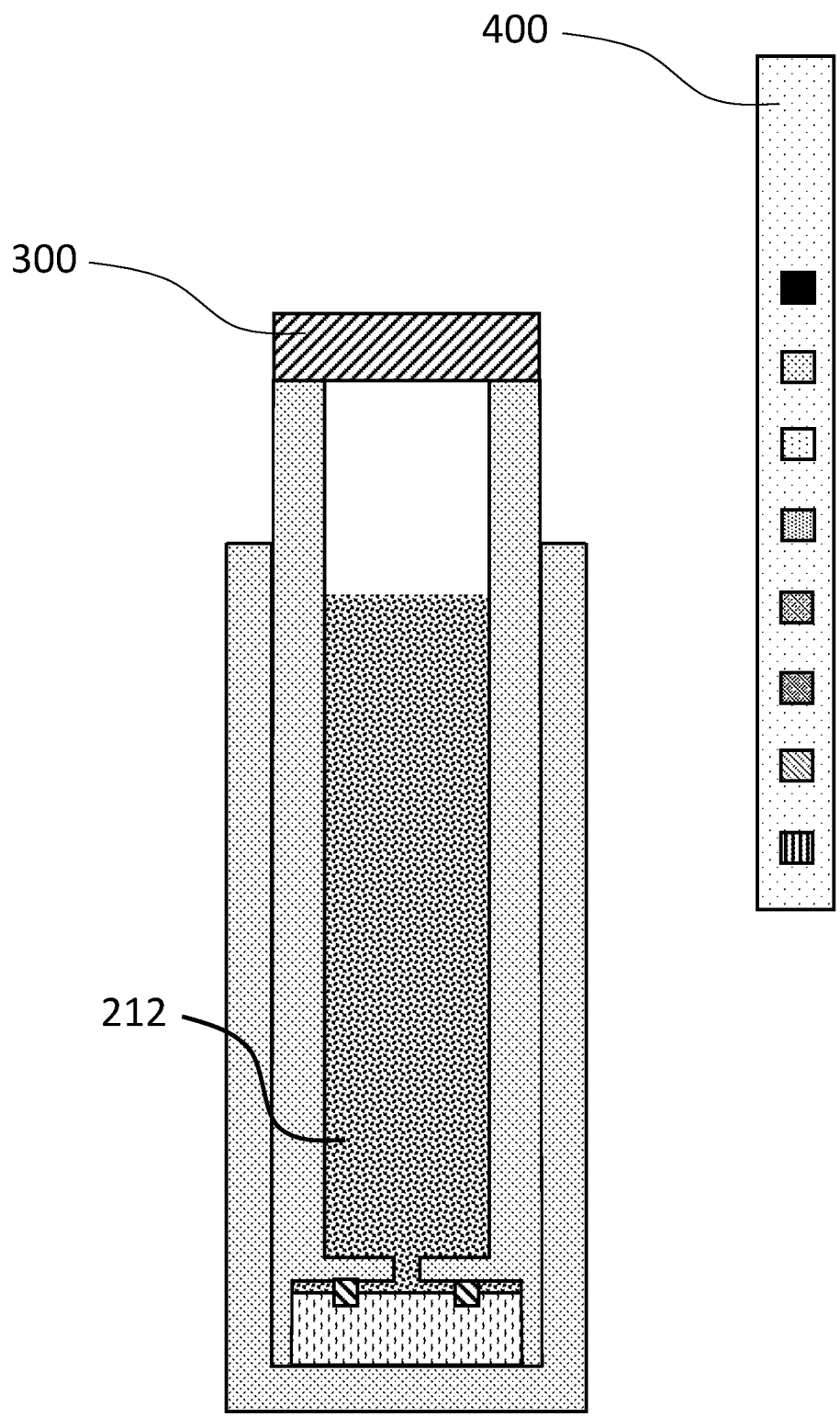
FIG. 6 is a side cross-sectional view of the liquid holding assembly of FIG. 5, in which the cap is closed after the removal of the test strip, in order to hold the liquid for further testing.
Figure 7:
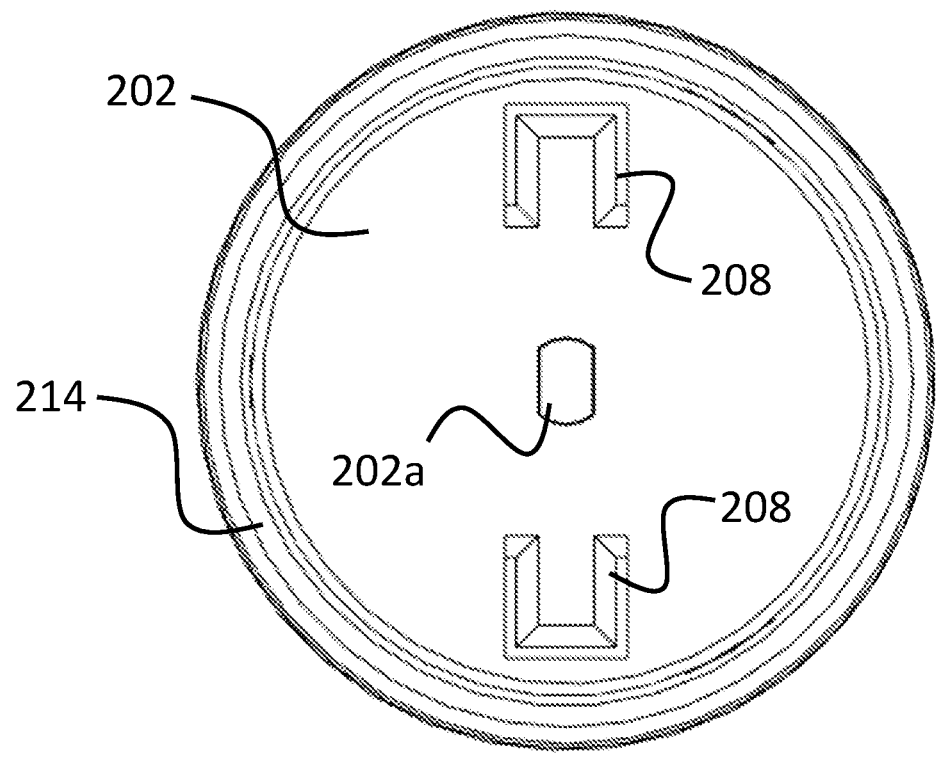
FIG. 7 is a bottom view of the second tube, showing a perforation and a holding unit, according to some embodiments of the present invention.
Figure 8:
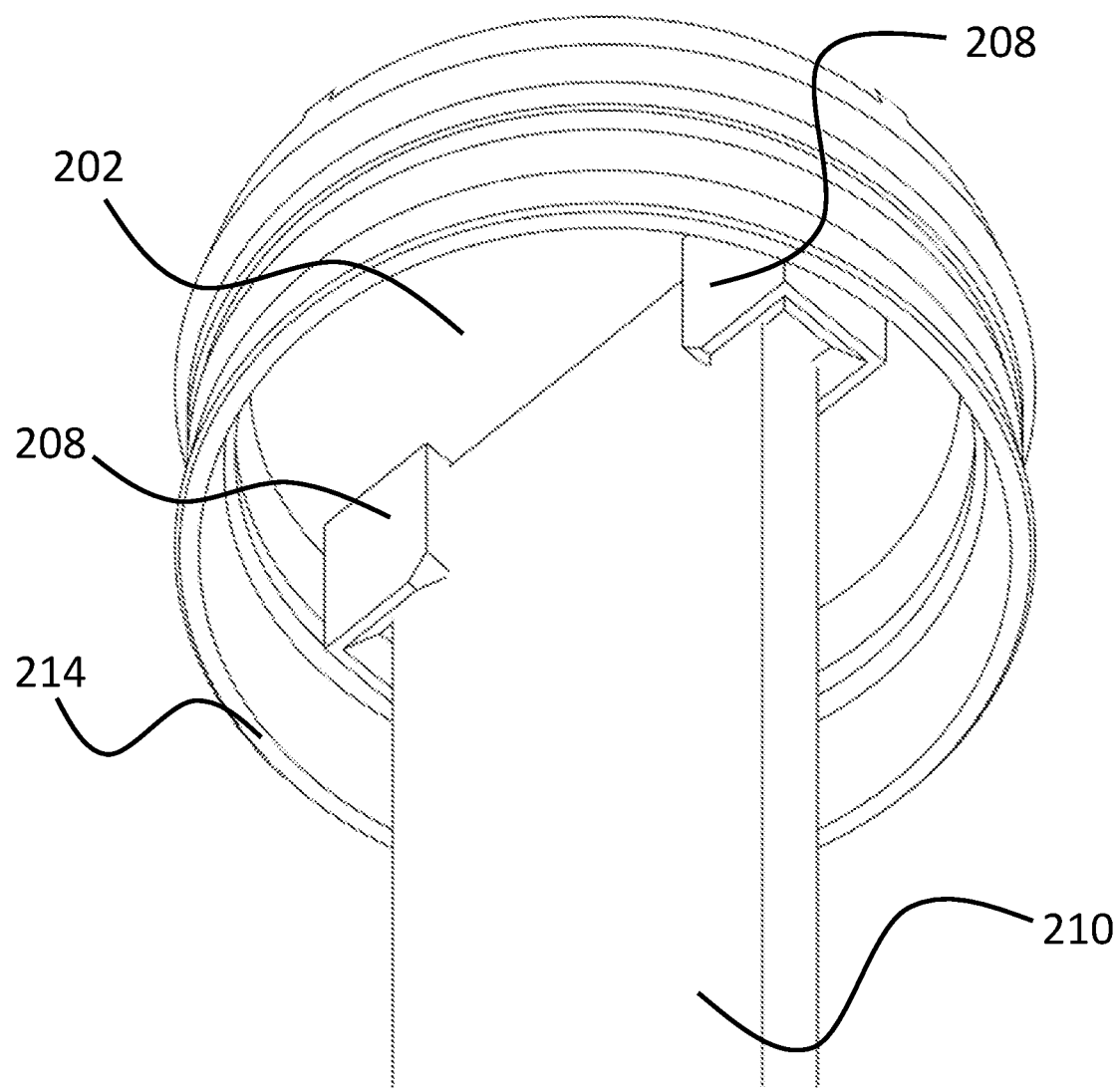
FIG. 8 is a perspective view of the bottom end of the second tube showing a perforation and a holding unit holding the sponge, according to some embodiments of the present invention.

FIG. 1 is a side cross-sectional view of a liquid holding assembly of the present invention, in which a first tube and a second tube are detached from each other. FIGS. 2-4 are side cross-section views of the liquid holding assembly of FIG. 1, in which the second tube is inserted into the first tube, such that a sponge held by the second tube is compressed between the first tube and the second tube and releases a liquid absorbed within the sponge into the second tube. FIG. 5 is a side cross-sectional view of the liquid holding assembly of FIGS. 1-4, in which a test strip is removed from the second tube via a cap, after the test strip has contacted the liquid, in some embodiments of the present invention. FIG. 6 is a side cross-sectional view of the liquid holding assembly of FIG. 5, in which the cap is closed after the removal of the test strip, in order to hold the liquid for further testing. FIG. 7 is a bottom view of the second tube, showing a perforation and a holding unit, according to some embodiments of the present invention. FIG. 8 is a perspective view of the bottom end of the second tube showing a perforation and a holding unit holding the sponge, according to some embodiments of the present invention.

The liquid holding assembly 10 includes a first tube 100 and a second tube 200. The first tube 100 has a closed first bottom end 102, an open first top end 104, and a first longitudinal wall 106 extending between the first bottom end 102 and the first top end 104. The first longitudinal wall encloses an inner cavity 108, and has an inner surface 106a and an outer surface 106b. The inner surface 106a faces the inner cavity 108, while the outer surface 106b faces outward from the first tube 100.

The second tube 200 is configured to be inserted in the first tube 100 via the open first top end 104. The second tub 200 has a closed second bottom end 202, a second top end 204, and a second longitudinal wall 206 extending between the second bottom end 202 and the second top end 204. The second bottom end 204 has a perforation 202a and includes a holding unit 208 configured to hold a sponge 210 below the second bottom end 202. Furthermore, the perimeter of the second bottom end 202 is configured to fit tightly against the inner surface 106a of the first longitudinal wall 106 when the second tube 200 is inserted into the first tube 100.

The sponge 210 is configured to absorb a liquid. The liquid may be any liquid that a user may need to collect for testing. The liquid may be, for example, urine. A user may hold the second tube 200 with the sponge 210 attached, to keep the sponge away from the user's hand, and urinate on the sponge (or have a patient urinate on the sponge) without soiling the user's hand.

Once the liquid is collected on the sponge 210, the second tube 200 is configured to be inserted into the first tube 100 to compress the sponge 210 between the first bottom end 102 of the first tube 100 and the second bottom end 202 of the second bottom tube 200, as seen in FIGS. 2-4.

The sponge 210 is configured to release the liquid 212 when compressed. A tight fit between the first longitudinal wall 106 and the perimeter of the second bottom end 202 is configured to prevent passage of the liquid 121 released by the sponge 208 into the first tube 100 above the perimeter of the second bottom end 202 of the second tube 200. In this manner, the liquid 212 released by the sponge 210 is forced to travel into the second tube 200 via the perforation 202a in the second bottom end 200, as seen in FIG. 4.

In some embodiments of the present invention, the second top end 204 extends above the first top end 104 when the second tube 200 is fully inserted into the first tube 100. In some embodiments of the present invention, the liquid holding assembly 100, includes a cap 300 covering the second top end 204 of the second tube 200. The cap 300 may be removably joined to the second tube, to enable access to the liquid 212 in the second tube 200 for testing, as seen in FIG. 5.

In some embodiments of the present invention, the second tube 200 is configured to hold a test strip 400. In this manner, the 212 liquid released by the sponge 210 when the sponge 210 is compressed between the first bottom end 102 the second bottom end 202 is forced to travel into the second tube 200 via the perforation 202a in the second bottom end 202 and to contact the test strip 400 in the second tube.

The test strip 400 includes one or more chemical pads 402 or reagents which react (change color) when immersed in, and then removed from, a liquid sample. If the liquid is urine, the test strip may include a standard test strip commonly used to test urine for the presence of proteins, glucose, ketones, hemoglobin, bilirubin, urobilinogen, acetone, nitrite and leucocytes, as well as testing of pH and specific gravity, or to test for infection by different pathogens. In a variant, the test strip may include a test strip used to test urine for the presence of one or more drugs, such as THC, COC, OXY, MDMA, BUP, MOP, AMP, BAR, BZO, MET, MTD, PCP ID-CP12-BUP (5), for example.

The cap 300 is configured to be opened to allow removal of the test strip 400 (as seen in FIG. 5). As shown in FIG. 6, the cap 300 is closed again to prevent the liquid 212 from spilling out of or escaping from the assembly 10. In this manner, the assembly 10 can be safely sent to a lab (by mail, for example) for testing of the liquid 212.

In some embodiments of the present invention, the assembly 10 of the present invention is provided as a kit which also includes the sponge 210 and the test strip 400. In this manner, a user can test the liquid (e.g., urine), remove the test strip 400 after the test strip has been in contact with the liquid, and send a photograph of the test strip 400 to a medical professional. Depending on the results shown by the test strip 400, the medical professional may request that the closed assembly 10 containing the liquid 212 be sent to a lab for further analysis. When the assembly 10 is closed, the tight contact between the first tube 100 and the second tube 200 and the closed cap 300 prevent escape of the liquid 212 from the assembly 10, allowing the assembly 10 to be safely mailed or transported to the lab.

In some embodiments of he the present invention, the second bottom end 202 includes a spacer unit 214 extending downward from a lower surface of the second bottom end 202 to create a hollow chamber between the first bottom end 102 and the second bottom end 202, where the compressed sponge 210 is housed, when the spacers 214 contact the first bottom end 102 and stop the motion of the second tube 200 into the first tube 100. The spacer unit 214 may include a plurality of distinct unit, or a single continuous wall.

Figure 9:
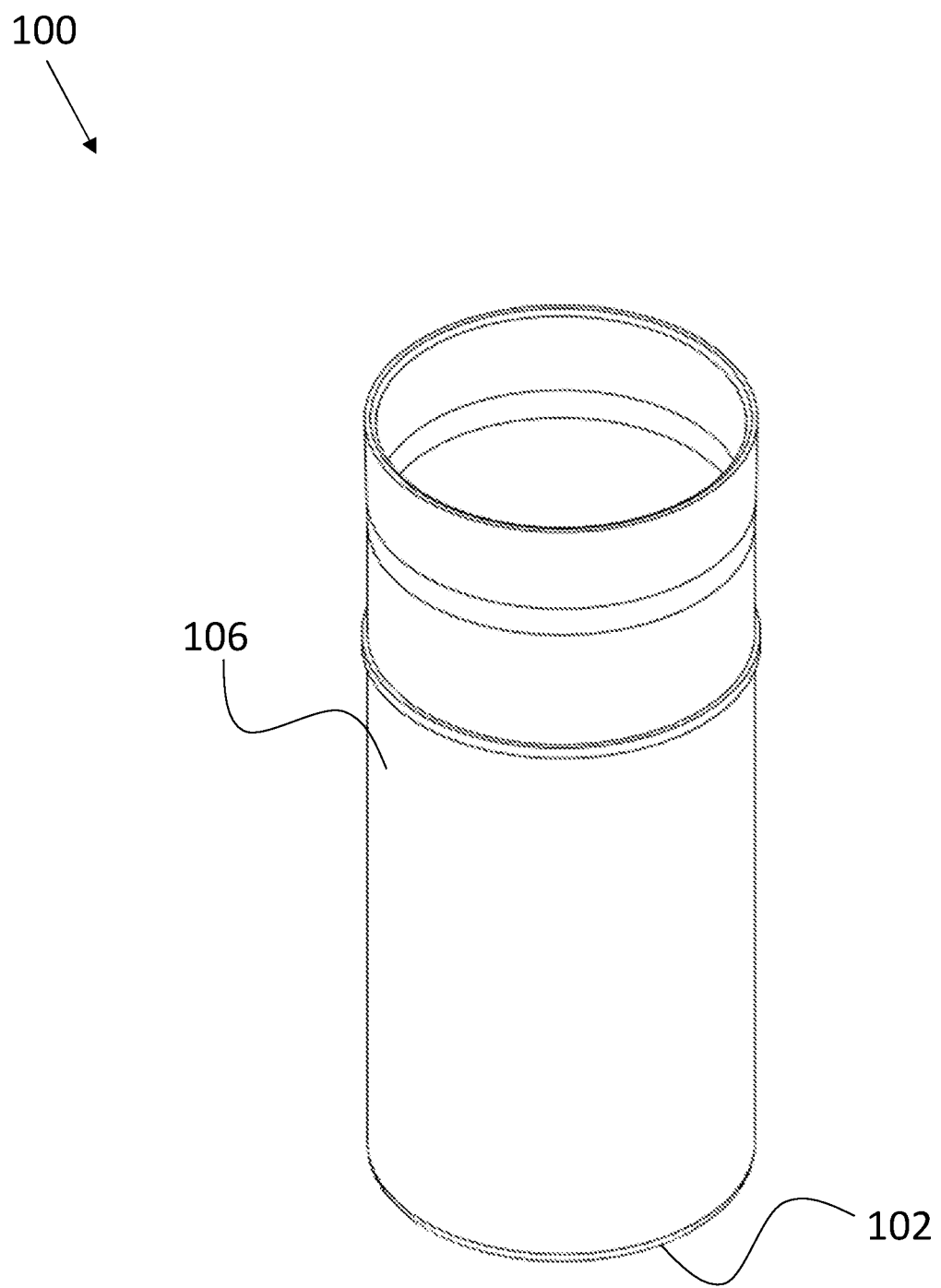
FIG. 9 is a perspective view of the first tube, according to some embodiments of the present invention.

FIG. 9 is a perspective view of the first tube 100, according to some embodiments of the present invention.

In some embodiment of the present invention, the first tub 100 is cylindrical, and the first longitudinal wall 106 is a hollow cylinder capped at the bottom by the first bottom end 102.

Figure 10:
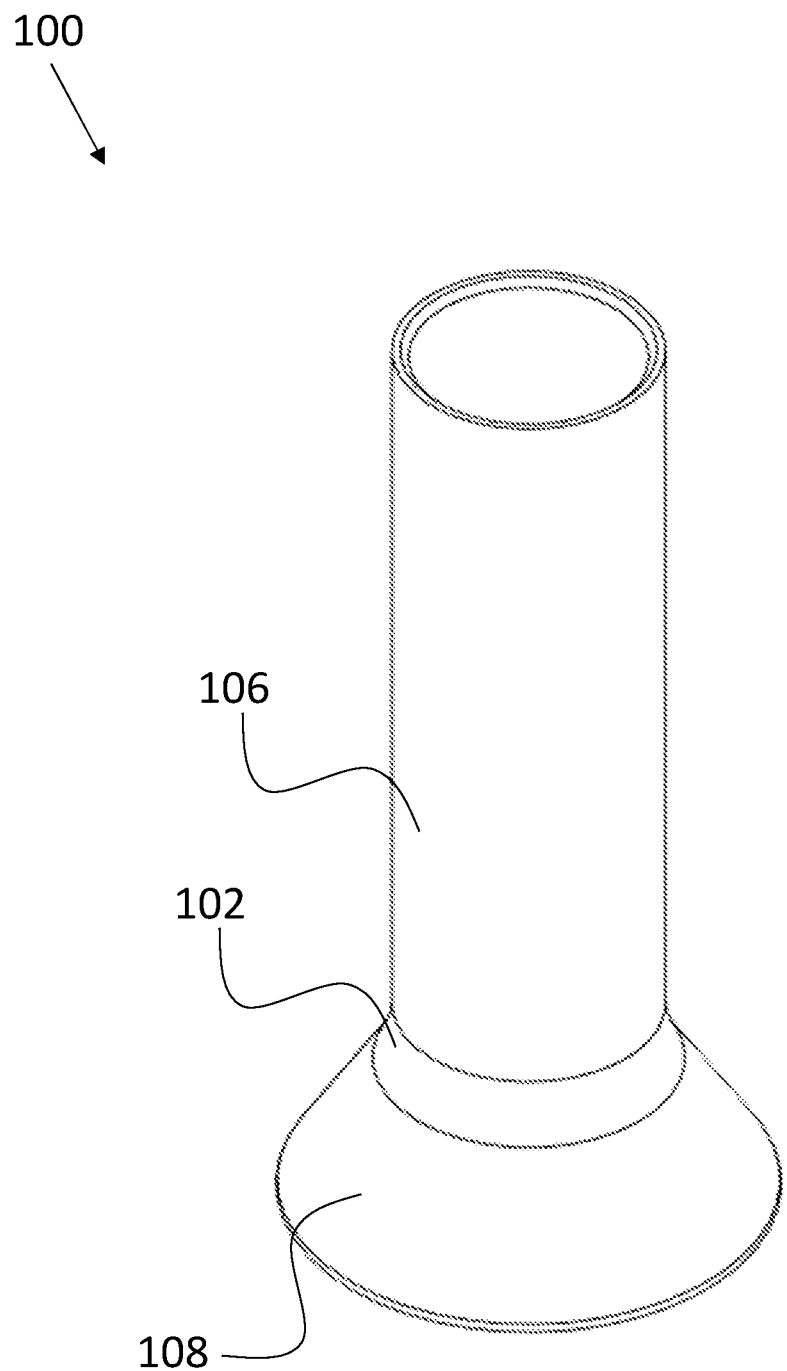
FIGS. 10 and 11 are perspective view of the first tube having a platform on the bottom thereof, according to some embodiments of the present invention.
Figure 11:
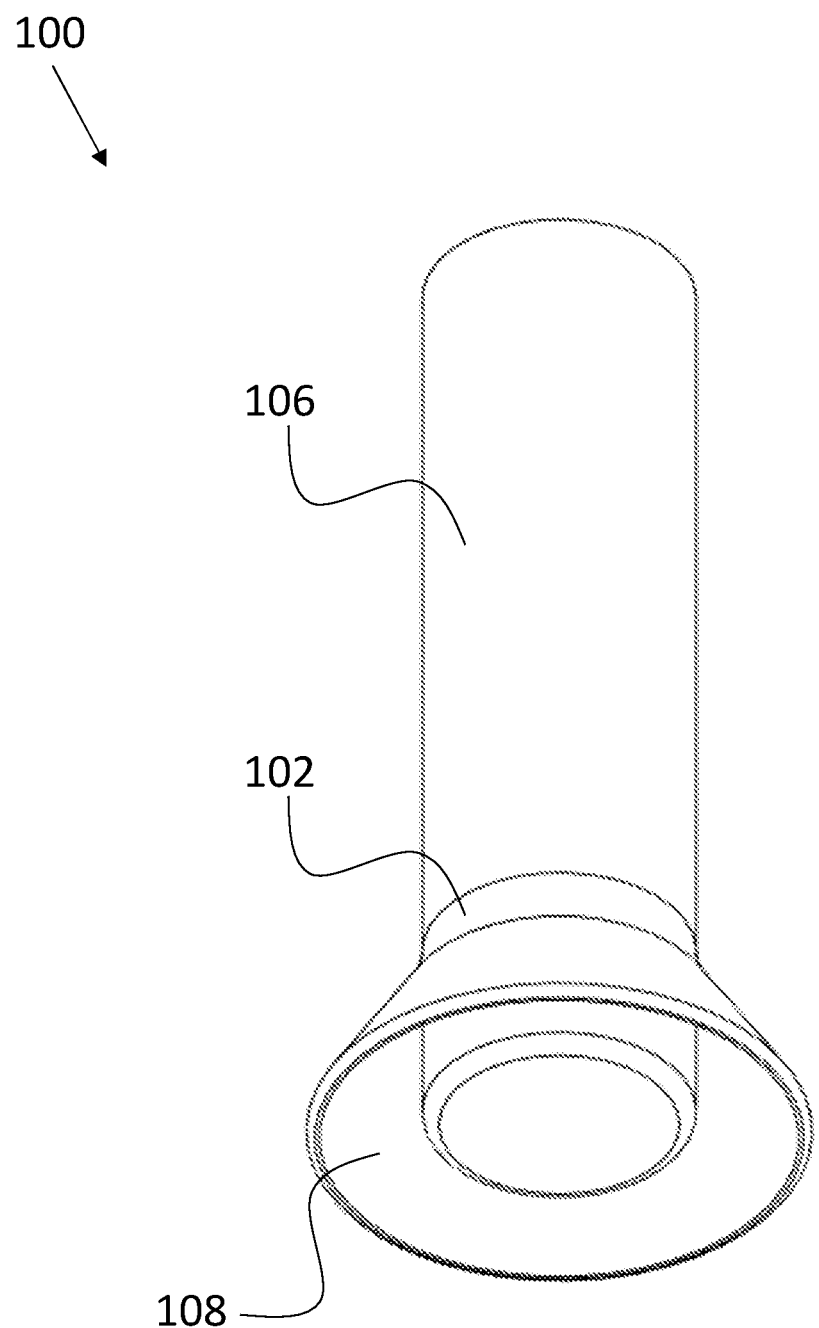

FIGS. 10 and 11 are perspective view of the first tube having a platform on the bottom thereof, according to some embodiments of the present invention.

In some embodiments of the present invention, first tube 100 includes a platform 108 below the first bottom end 102. Optionally, the platform 108 widens as the platform 108 extends away from the first bottom end 102. The platform enhance the stability of the first tube 100 (and of the assembly 10 as a whole), and therefore decreasing the chance of the first tube 100 tipping.

Figure 12A:
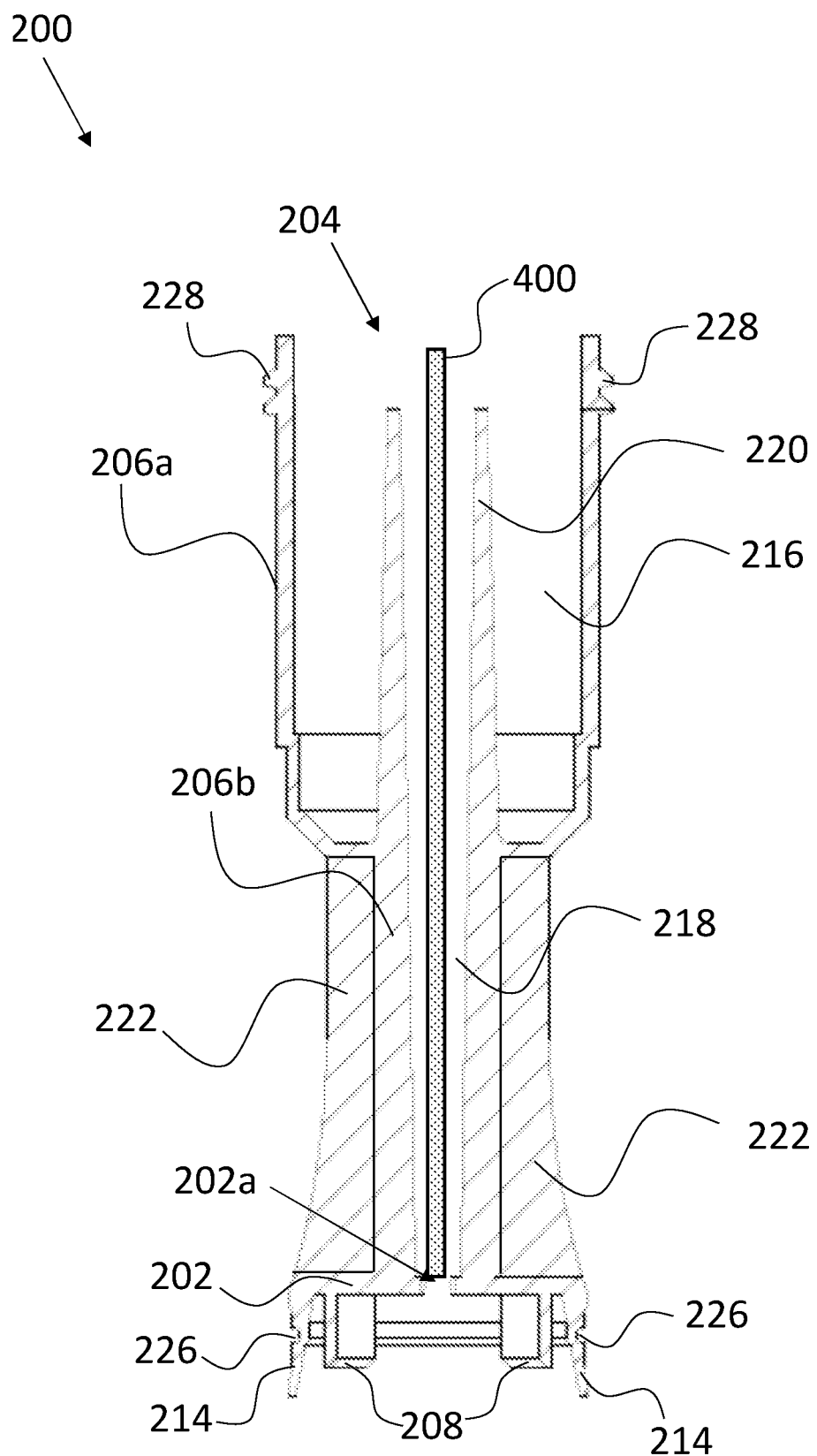
FIGS. 12a and 12b is a side cross sectional view of the threaded second tube having an upper reservoir and a channel below the upper reservoir, according to some embodiments of the present invention.
Figure 12B:
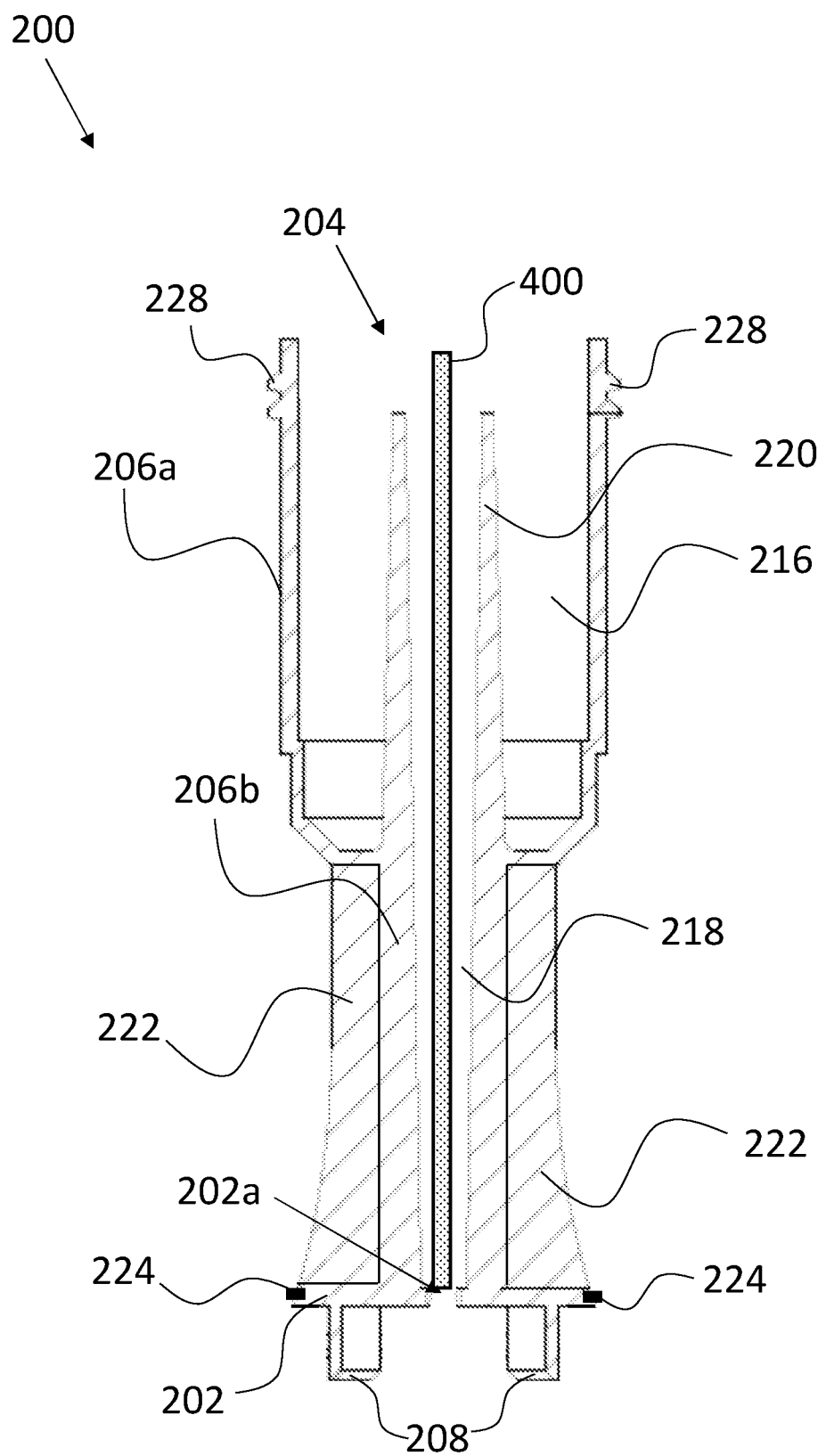
Figure 13:
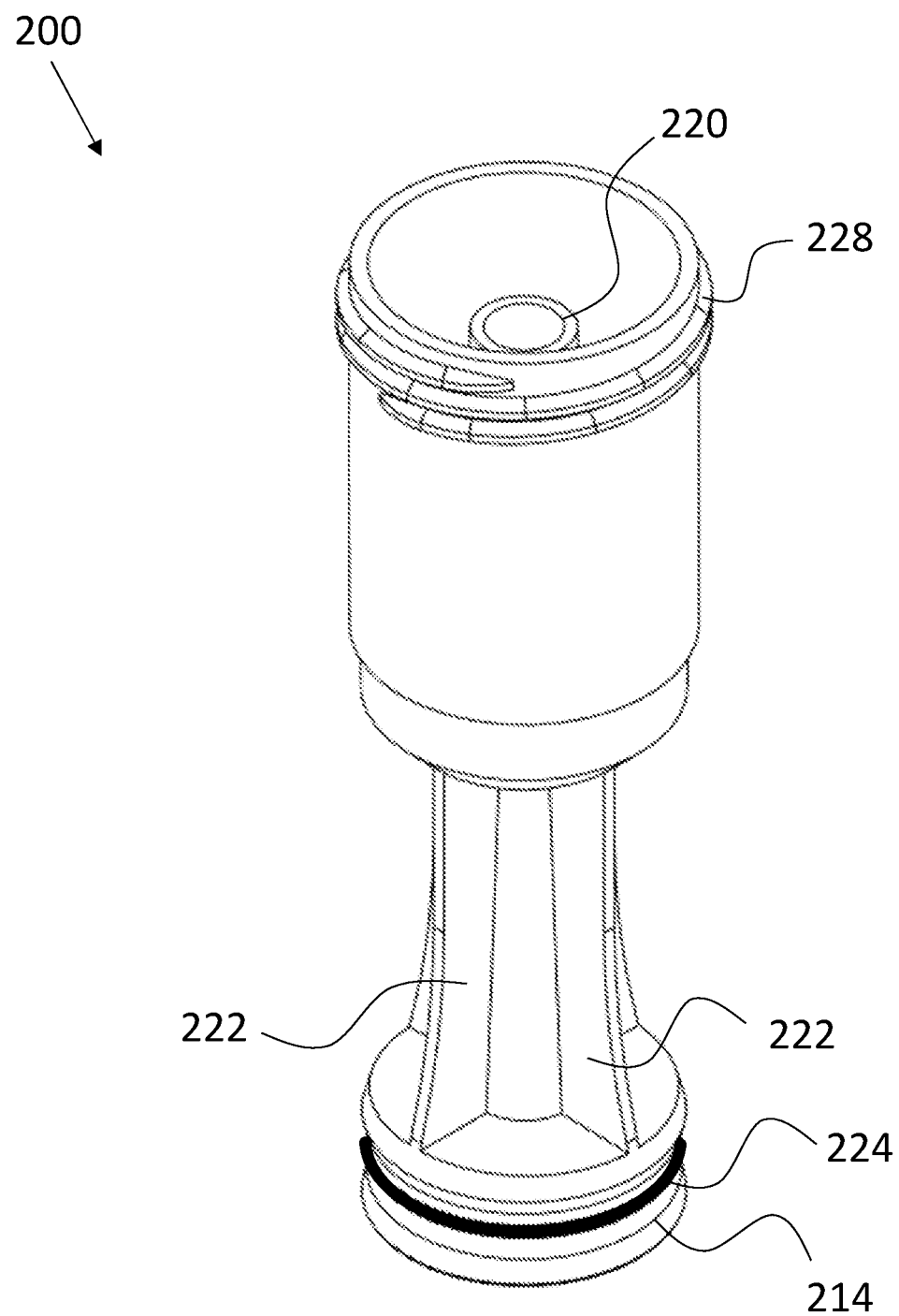
Figure 14:
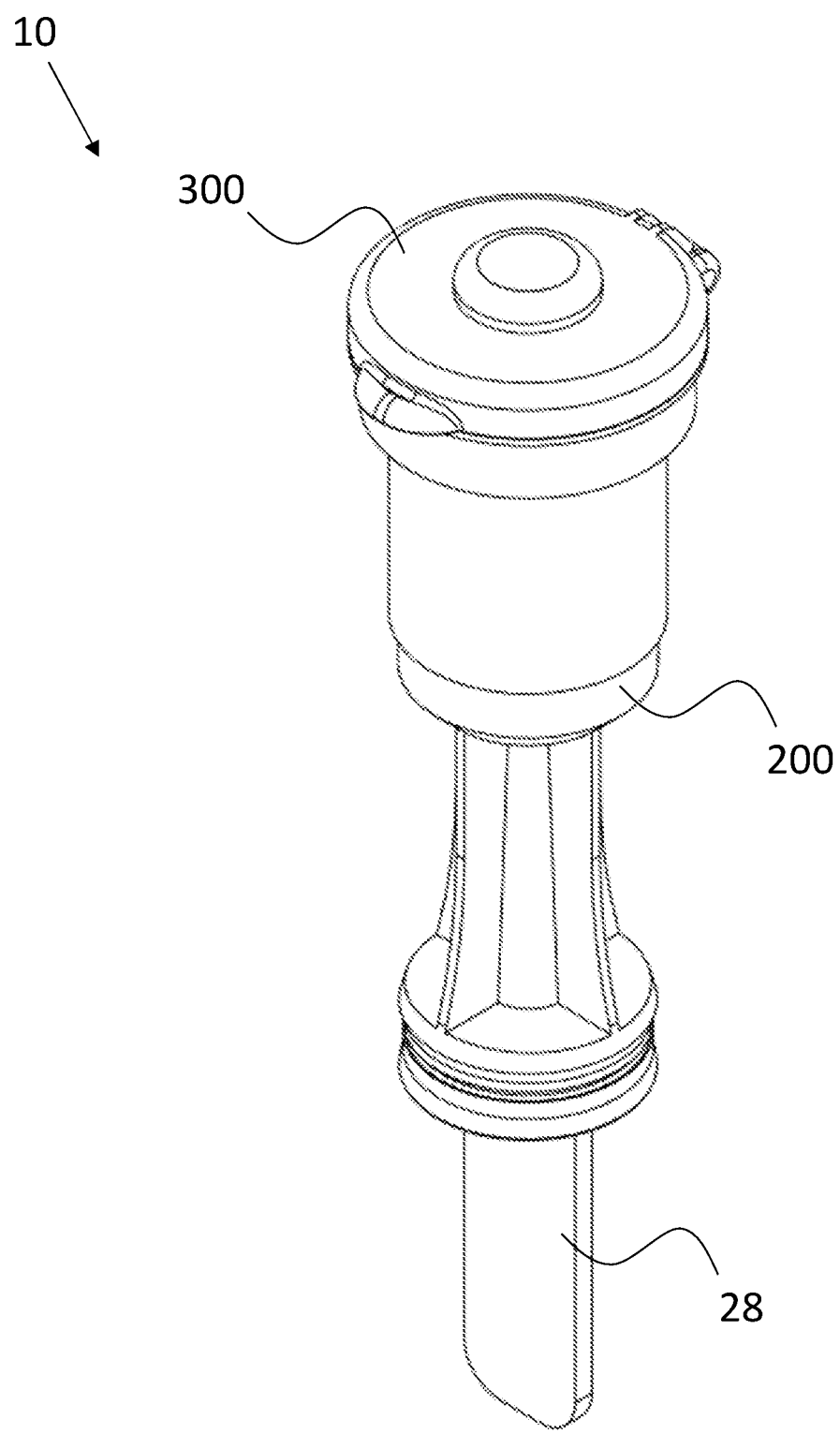
FIG. 14 is a perspective view of the threaded second tube of FIGS. 12a and 13 with a cap joined to the top end of the second tube, according to some embodiments of the present invention.
Figure 15:
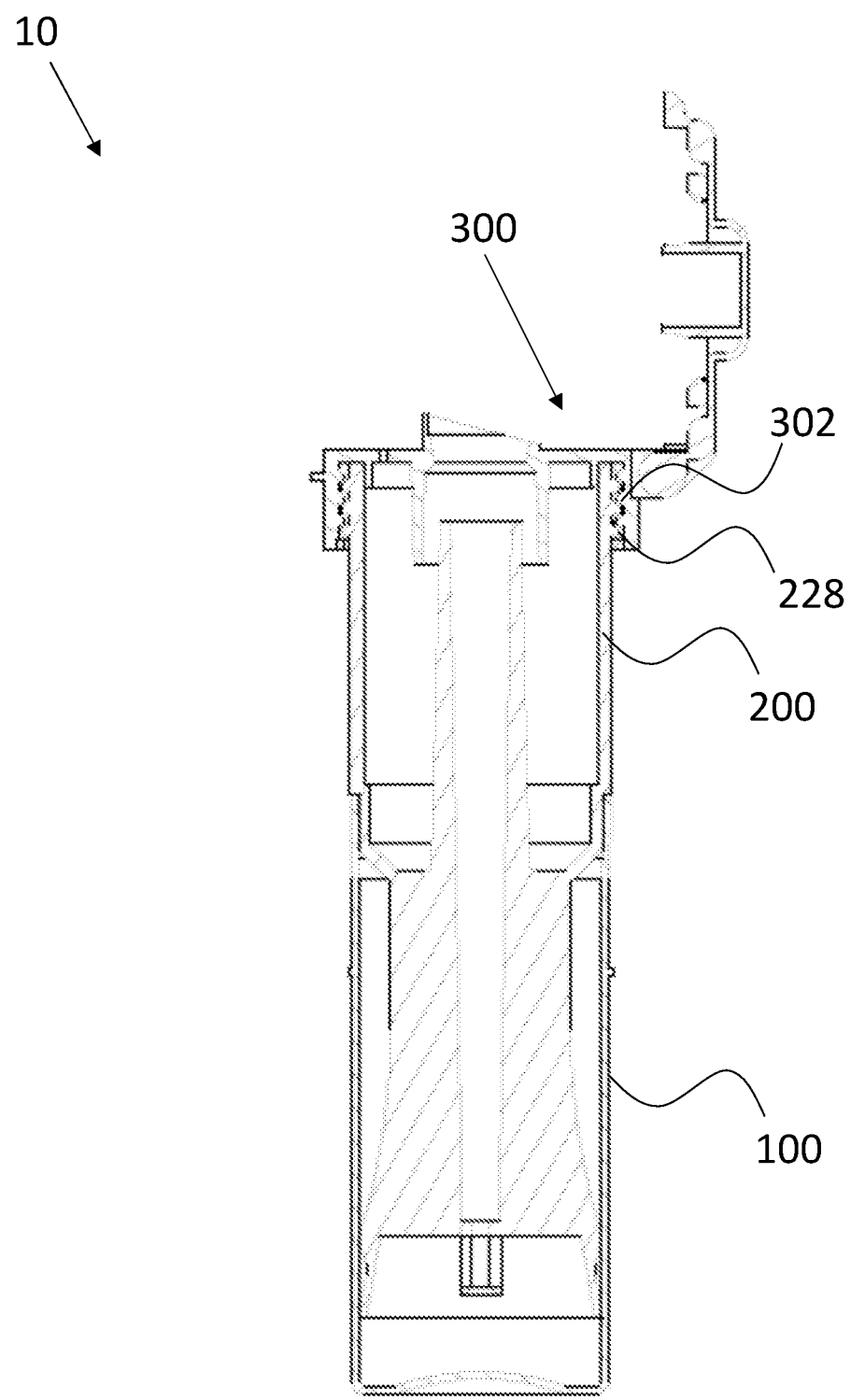
FIG. 15 is a side cross-sectional view of the liquid holding assembly with a threaded cap, according to some embodiments, of the present invention.
Figure 16:
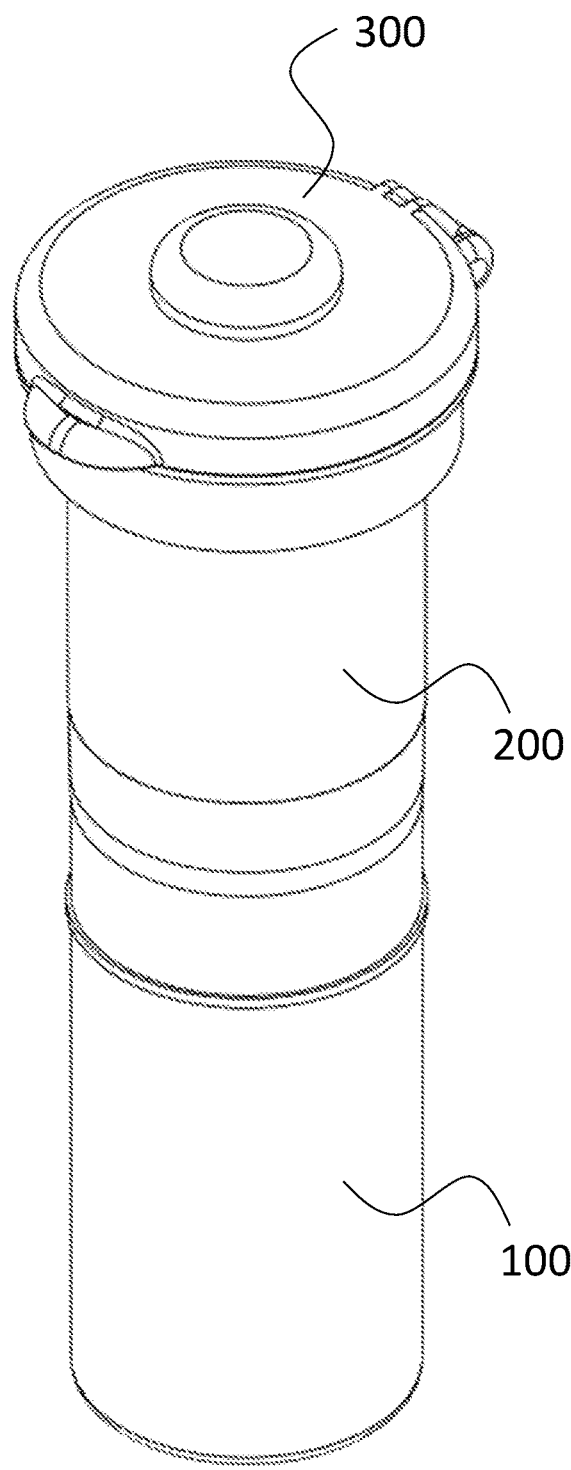
FIG. 16 is a perspective view of the liquid holding assembly of FIG. 15.

FIGS. 12a and 12b are a side cross sectional view of the threaded second tube having an upper reservoir and a channel below the upper reservoir, according to some embodiments of the present invention. FIG. 13 is a perspective view of the threaded second tube of FIG. 12a. FIG. 14 is a perspective view of the threaded second tube of FIGS. 12a and 13 with a cap joined to the top end of the second tube, according to some embodiments of the present invention. FIG. 15 is a side cross-sectional view of the liquid holding assembly with a threaded cap, according to some embodiments, of the present invention. FIG. 16 is a perspective view of the liquid holding assembly of FIG. 15.

In the embodiment of FIG. 12a, the second tube 200 includes the extender 214. In the embodiment of FIG. 12b, the second tube 200 does not include the extender 214.

In some embodiments of the present invention, the second tube includes an upper reservoir 216 and a channel 218. The upper reservoir is located below the second top end 204 and is surrounded by an upper portion 206a of the second longitudinal wall. The channel 218 located between the upper reservoir 216 and above the second bottom end 202, and is surrounded by a lower portion 206b of the second longitudinal wall. The channel 218 is in fluid communication the upper reservoir 216 and with the perforation 202a at the second bottom end 202. The channel 218 is optionally radially narrower than the upper reservoir 216 and the second bottom end 202

In some embodiments, the channel 218 is sized to contain a portion of the test strip and to keep the portion of the test strip 400 substantially parallel to a central axis of the second tube. In some embodiments of the present invention, the channel 218 extends partially into the upper reservoir 216 via a wall extension 220 inside the upper reservoir 220. The channel 218 is still in fluid communication with the upper reservoir 216, so that liquid released by the sponge travels through the channel 218 to contact the test strip 400, and spills into the upper reservoir 216 after reaching the top end of the wall extension 220.

In some embodiments of the present invention, the second tube 200 incudes at least two panels 222 extending radially from an outer surface of the channel's lower portion 206b of the second longitudinal wall between the upper reservoir 216 and second bottom end 202. The panels 222 provide structural strength to the second tube 200 in a region where the narrower channel may structurally weaker.

In some embodiments of the present invention, the second bottom end 202 is in the form of a flat platform having a non-zero longitudinal height. In some embodiments of the present invention, the second bottom 202 end is radially surrounded by a sealing ring 224 to enhance the tight fit between the first longitudinal wall and the second bottom end, as seen in FIG. 12b.

In some embodiments of the present invention, the sealing the extender 214 is in the form of a wall which includes a groove 226 for holding the sealing ring, as shown in FIG. 12a. The sealing ring surrounding the extender 214 is shown in FIG. 13.

In some embodiment of the present invention an upper section of the second longitudinal wall comprises first threads 228. The cap 300 comprises second threads 302 configured to cooperate with the first threads 228. The cap 300 is configured to be joined to the second tube 200 by screwing the cap 300 onto the upper section of the second longitudinal wall.

Figure 17:
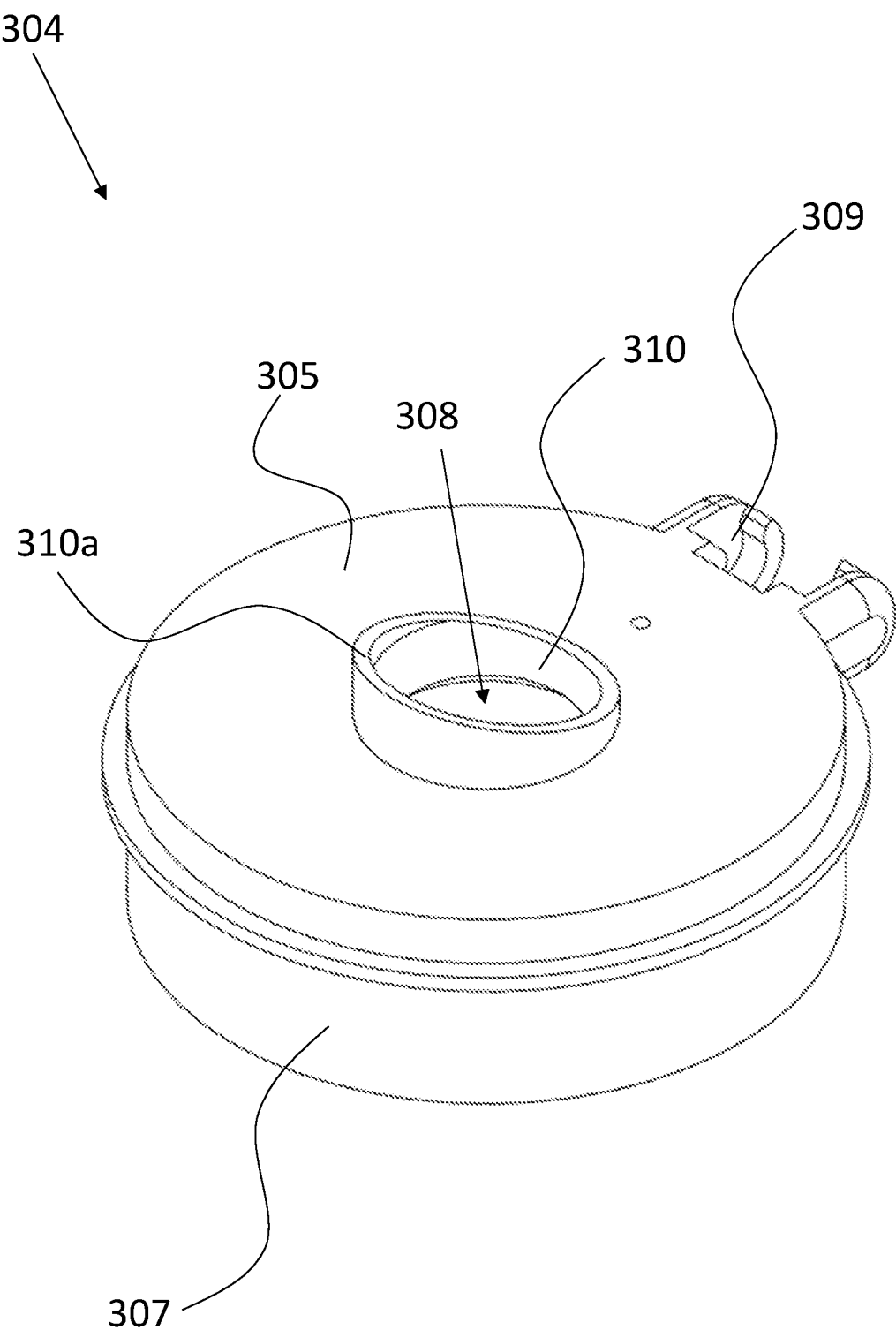
FIG. 17 is a perspective view of a cover portion of a threaded cap according to some embodiments of the present invention.
Figure 18:
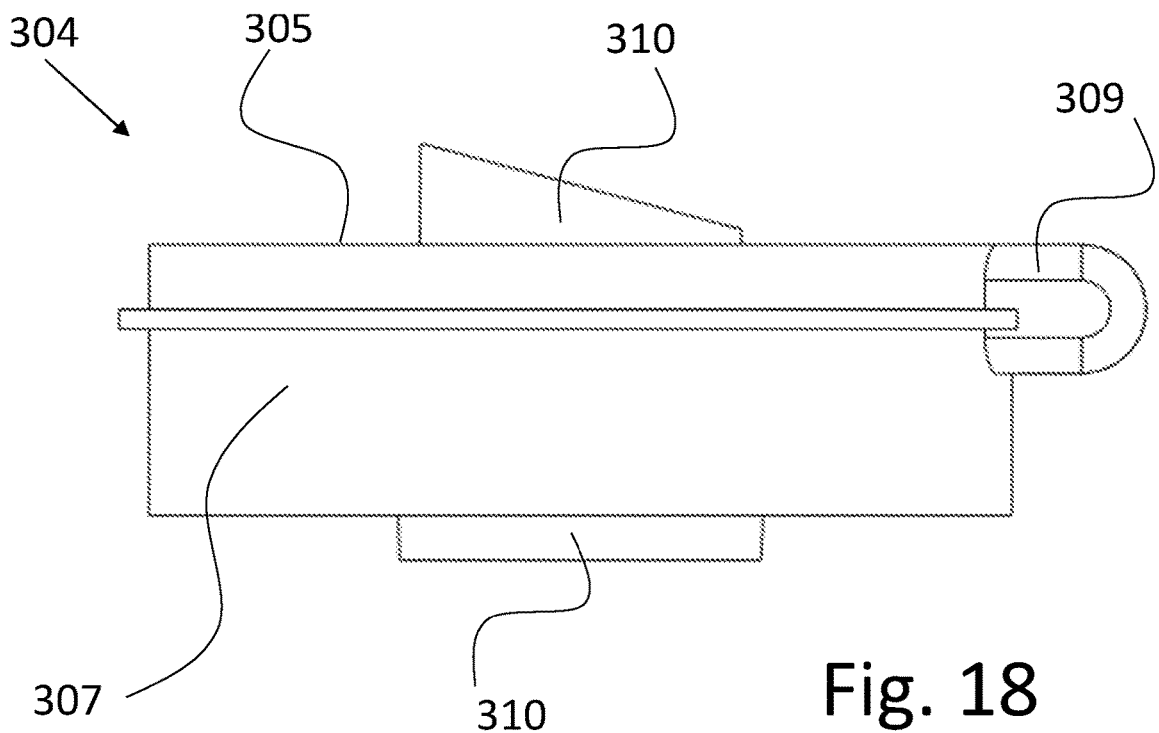
FIG. 18 is a side view of the cover portion of the threaded cap of FIG. 17.
Figure 19:
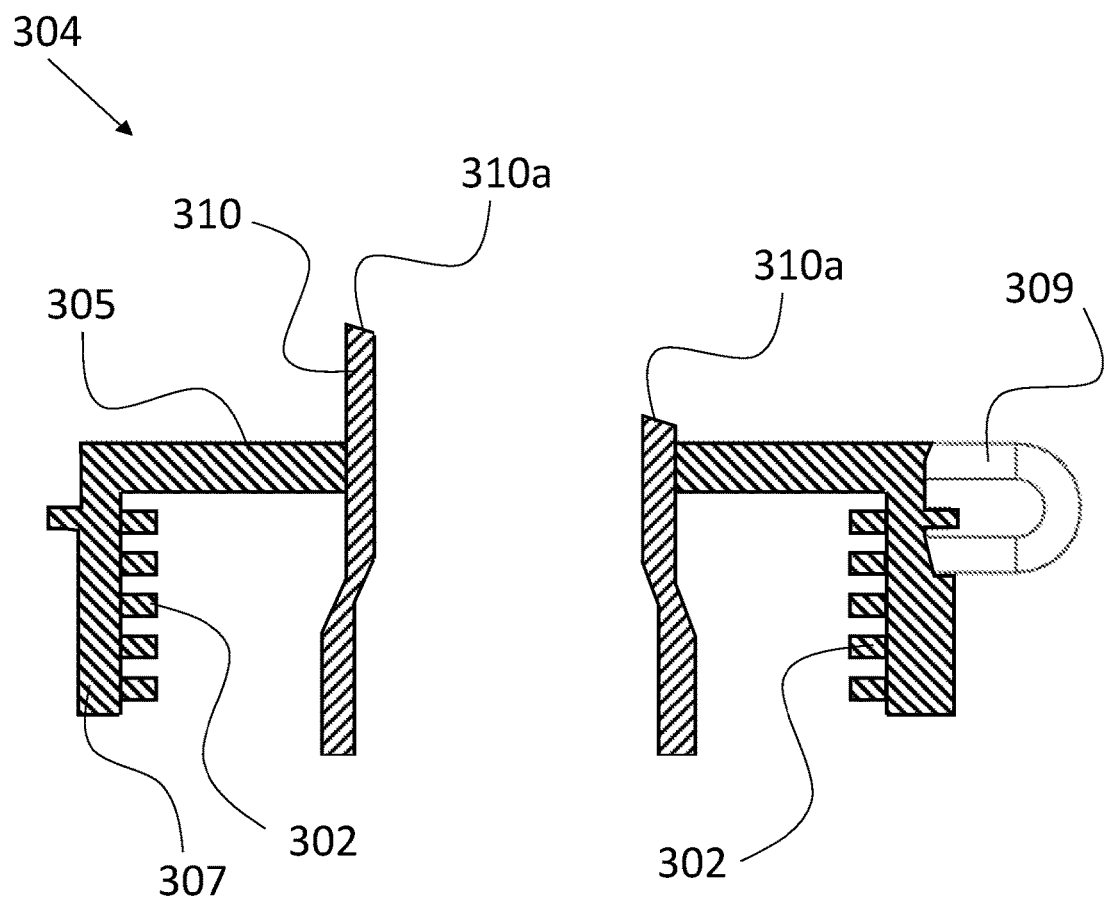
FIG. 19 is a side cross sectional view of the cover portion of the threaded cap of FIG. 17.
Figure 20:
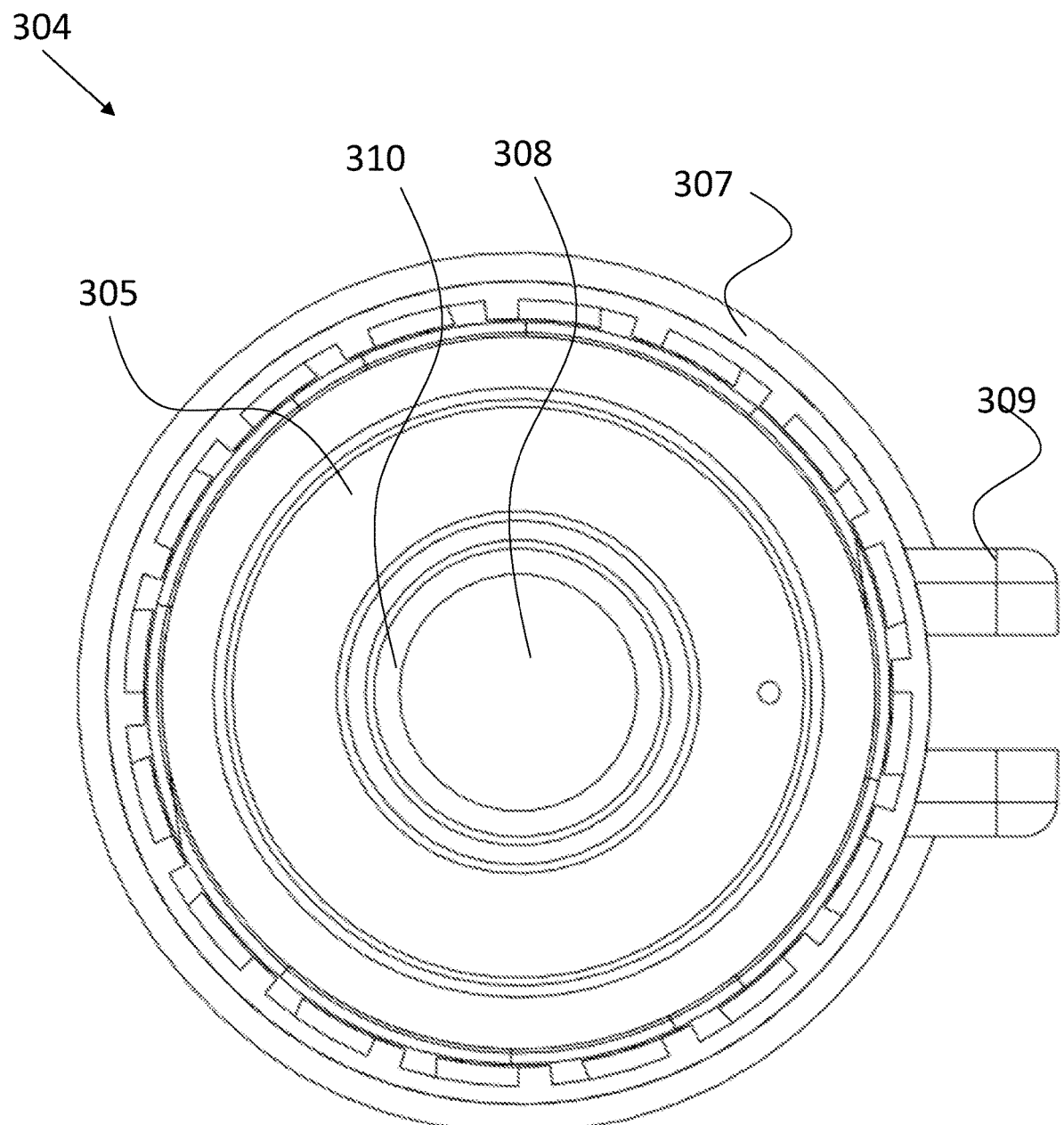
FIG. 20 is a bottom view of the cover portion of the threaded cap of FIG. 17.
Figure 21:
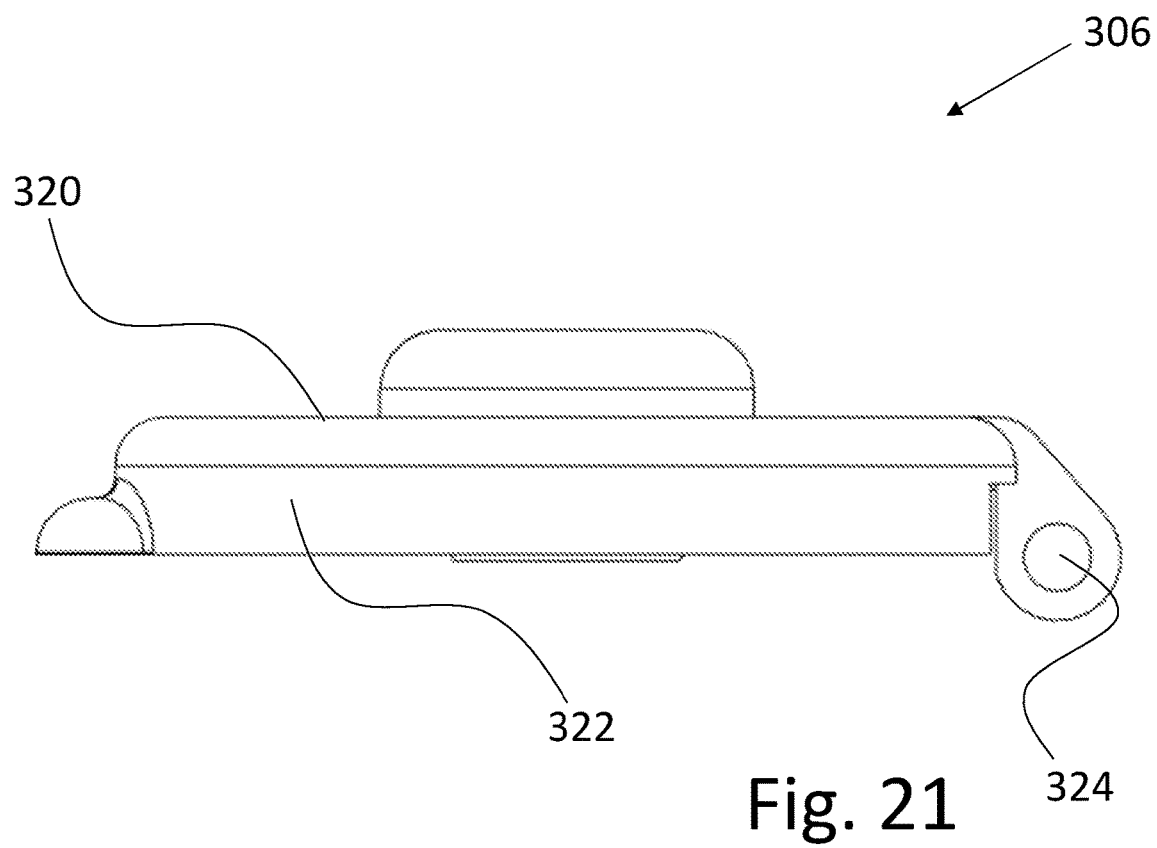
FIG. 21 is a side view of a lid of the threaded cap, according to some embodiments of the present invention.
Figure 22:
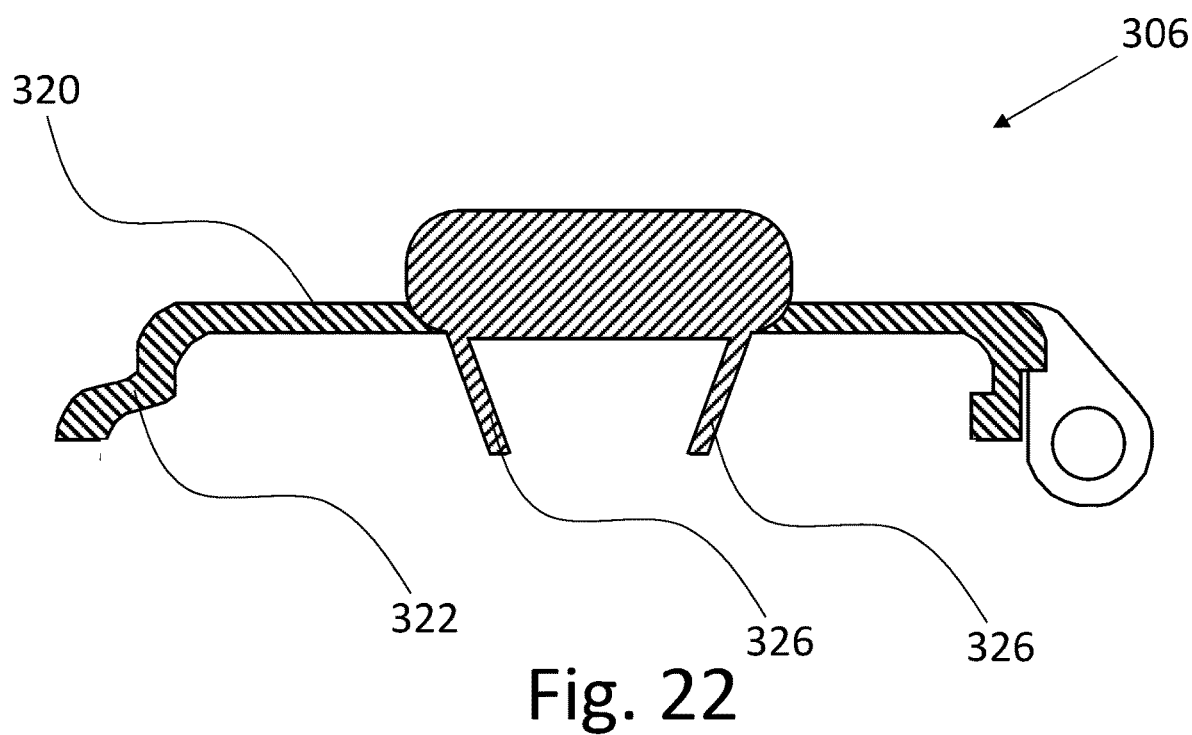
FIG. 22 is a side cross-sectional view of the lid of the threaded cap of FIG. 21.
Figure 23:
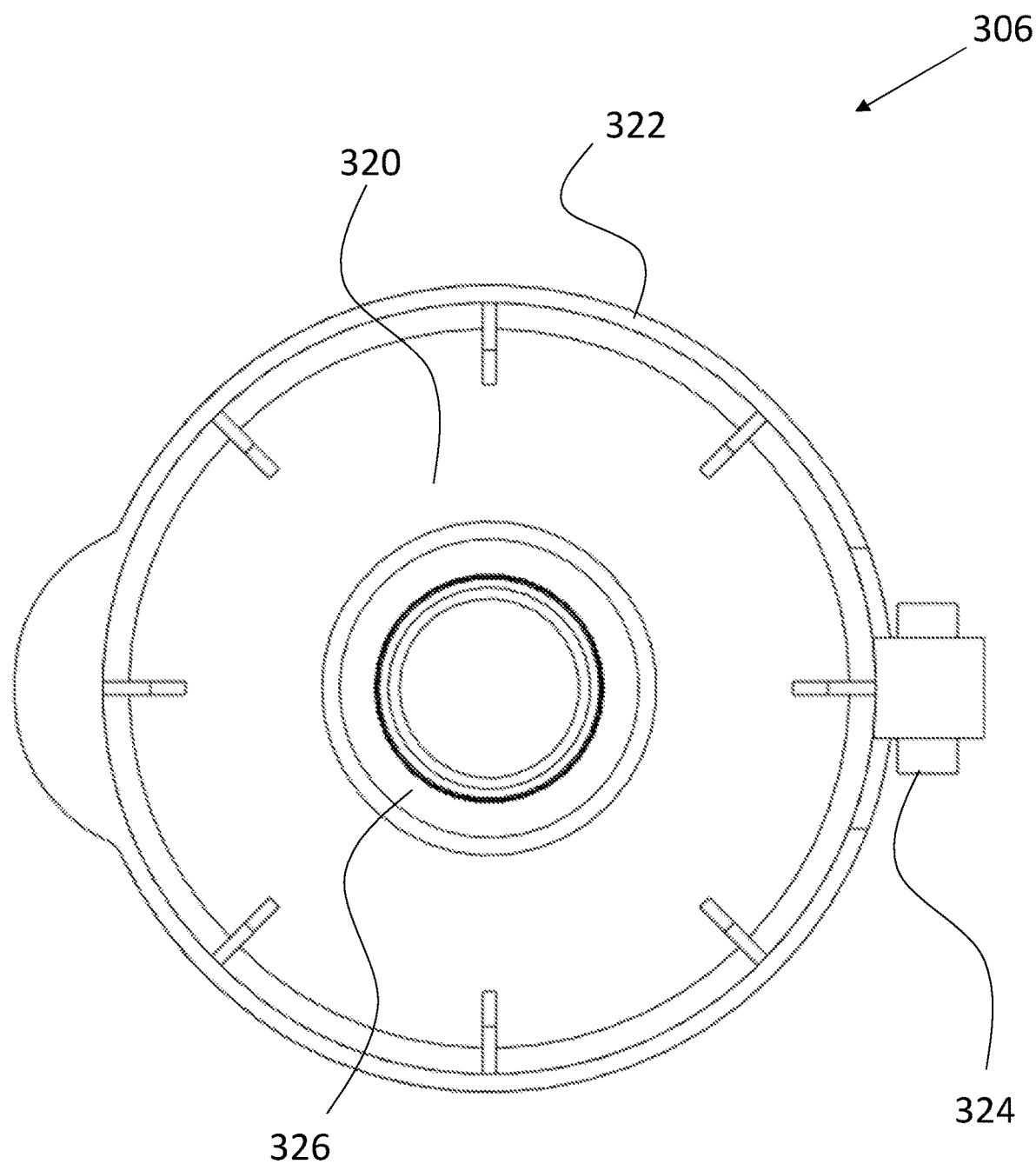
FIG. 23 is a bottom view of the lid of the threaded cap of FIG. 21.
Figure 24:
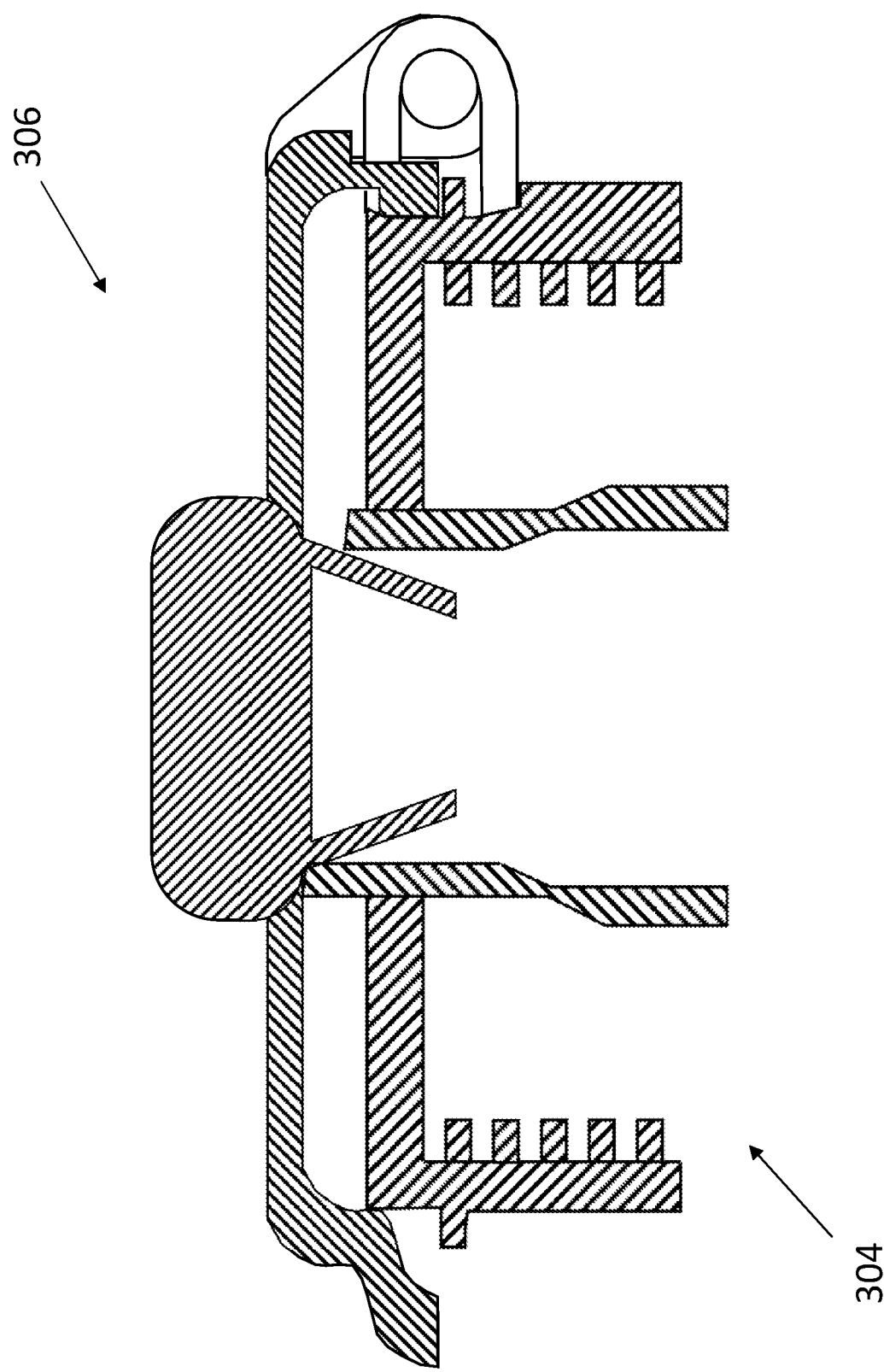
FIG. 24 is a cross sectional view of the threaded cap of FIG. 21, when lid cooperates with the cover portion.

FIG. 17 is a perspective view of a cover portion of a threaded cap according to some embodiments of the present invention. FIG. 18 is a side view of the cover portion of the threaded cap of FIG. 17. FIG. 19 is a side cross sectional view of the cover portion of the threaded cap of FIG. 17. FIG. 20 is a bottom view of the cover portion of the threaded cap of FIG. 17. FIG. 21 is a side view of a lid of the threaded cap, according to some embodiments of the present invention. FIG. 22 is a side cross-sectional view of the lid of the threaded cap of FIG. 21. FIG. 23 is a bottom view of the lid of the threaded cap of FIG. 21. FIG. 24 is a cross sectional view of the threaded cap of FIG. 21, when lid cooperates with the cover portion.

In some embodiments of the present invention, the cap 300 includes a cover 304 and a lid 306. The cover 304 has an upper panel 305 and an enclosure 307. The upper panel 205 covers the second top end 204 of the second tube 200 and has a second perforation 308. The enclosure 307 extends downward from the upper panel 305 and has an open lower end. The enclosure 307 is in the form of a cylindrical wall having second threads 302 on an inner surface thereof. The cover 304 includes a hinge holder 309 for holding a hinge of the lid 306. The cover 304 includes a duct 310 extending around and above the second perforation 308. The duct may also extend below the second perforation 308. The duct 310 has an upper rim 310a. In some embodiments of the present invention, the upper rim 310a is sloped so that the upper rim 310a is lowest near the hinge holder 309 and highest at its location that is farthest from the hinge holder 309.

The cover 304 is joined to the second tube so that the enclosure 307 surrounds the upper section of the second longitudinal wall, such that the second threads 302 cooperate with the first threads of the second tube.

The lid 306 includes a ceiling 320, a barrier 322, a hinge 324, and a stopper 326. The barrier 322 is a wall that extends downwards from the ceiling. The hinge 324 cooperates with the hinge holder 309, such that the lid 306 is hingedly joined to the cover 304. The stopper 326 extends downwards from a middle section of the ceiling 302. When the lid 306 closes the cover 304, the stopper 326 cooperates with the duct 310 to plug the second perforation 308 and prevent spillage of the liquid from the second tube, as seen in FIG. 24.

In some embodiments, a top portion of the test strip extends out of the second perforation 308 in the duct 310 to enable removal of the test tube without removal of the cap 300.

Figure 25:
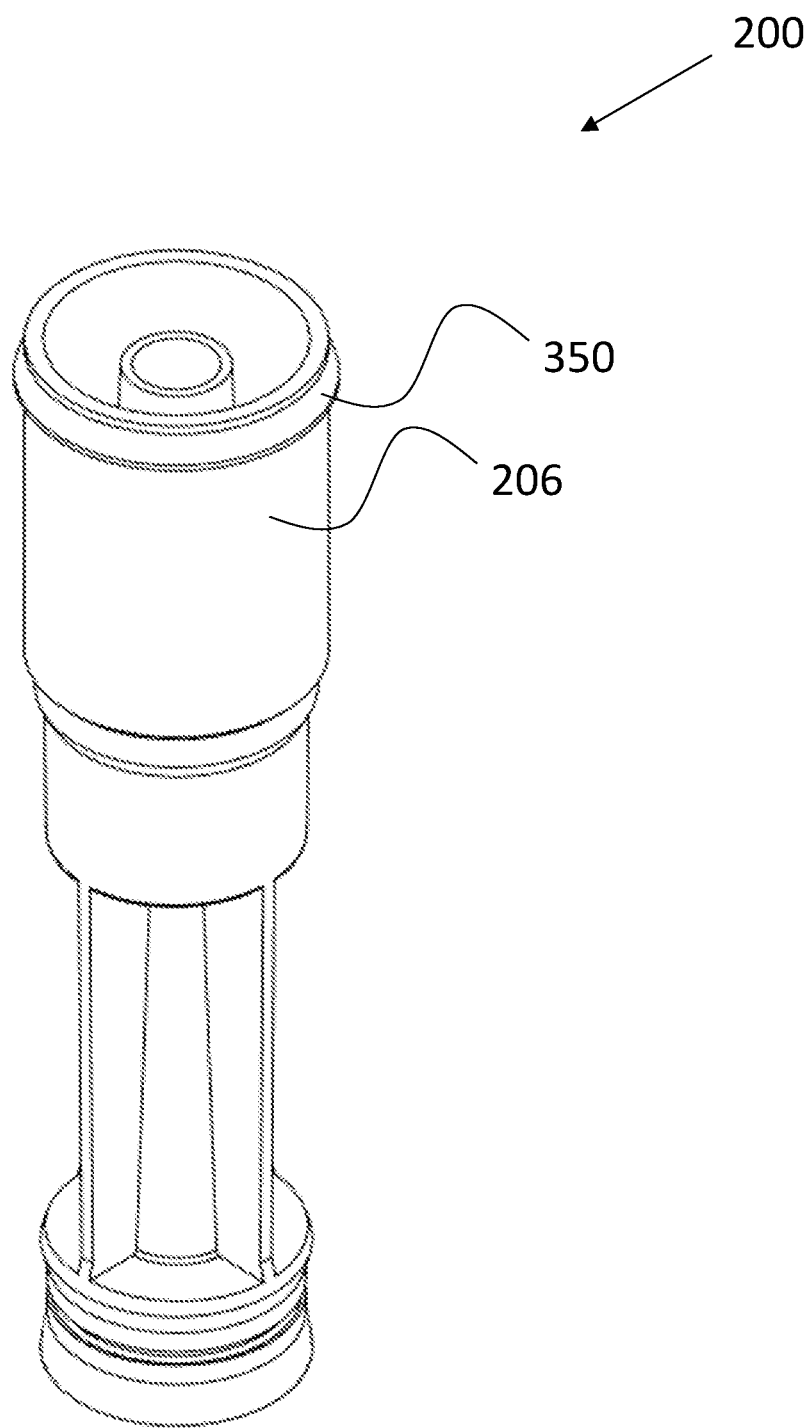
FIG. 25 is a perspective view of a rimmed second tube, according to some embodiments of the present invention.
Figure 26:
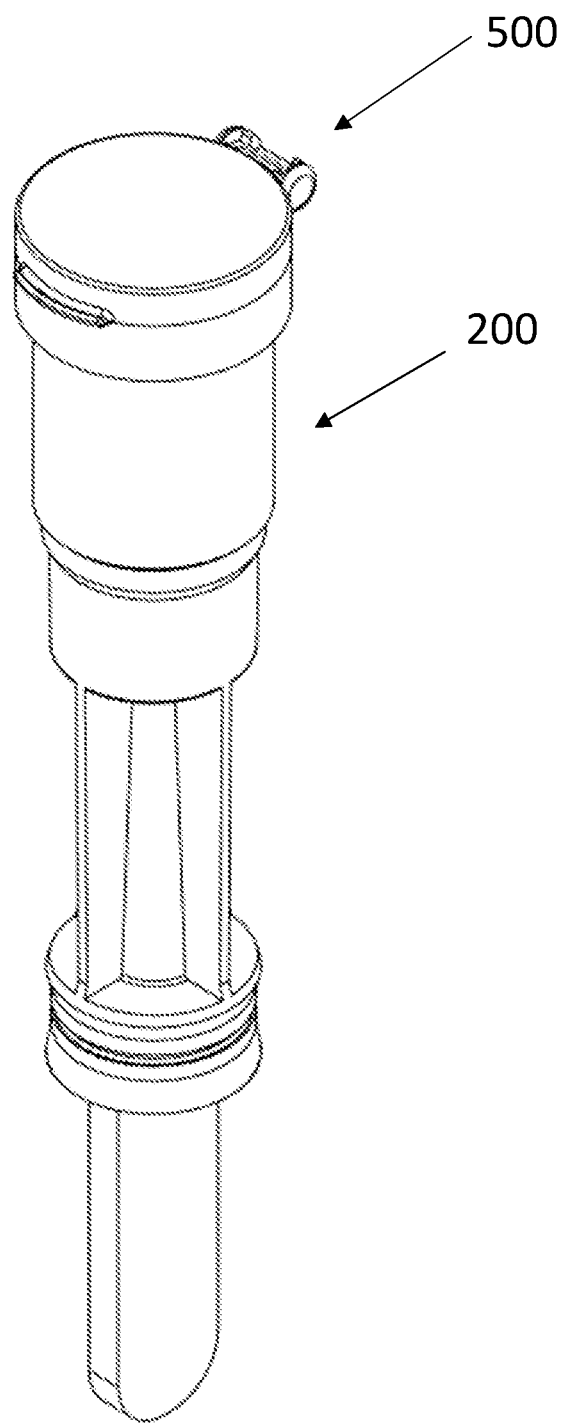
FIG. 26 is a perspective view of the rimmed second tube of FIG. 25 joined to a cap.

FIG. 25 is a perspective view of a rimmed second tube 200, according to some embodiments of the present invention. FIG. 26 is a perspective view of the rimmed second tube 200 of FIG. 25 joined to a cap 500.

In some embodiments of the present invention the upper section of the second longitudinal wall 206 of the second tube 200 includes a lip 250 extending radially outward from the outer surface of the second longitudinal wall, instead of the previously-described threads. The lip 350 may slope downward.

Figure 27:
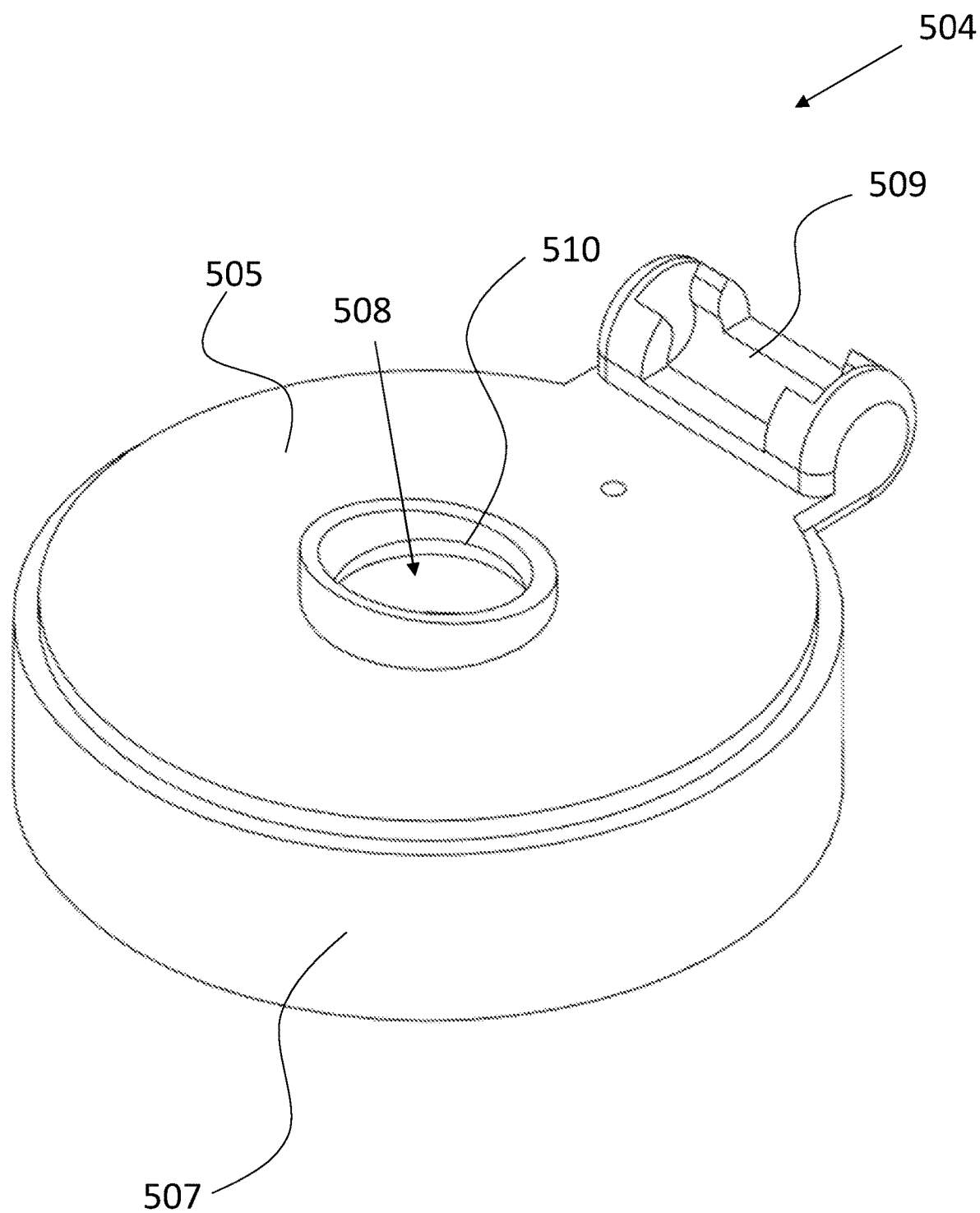
FIG. 27 is a perspective view of a cover portion of a cap configured for snapping to the rimmed second tube of FIG. 25, according to some embodiments of the present invention.
Figure 28:
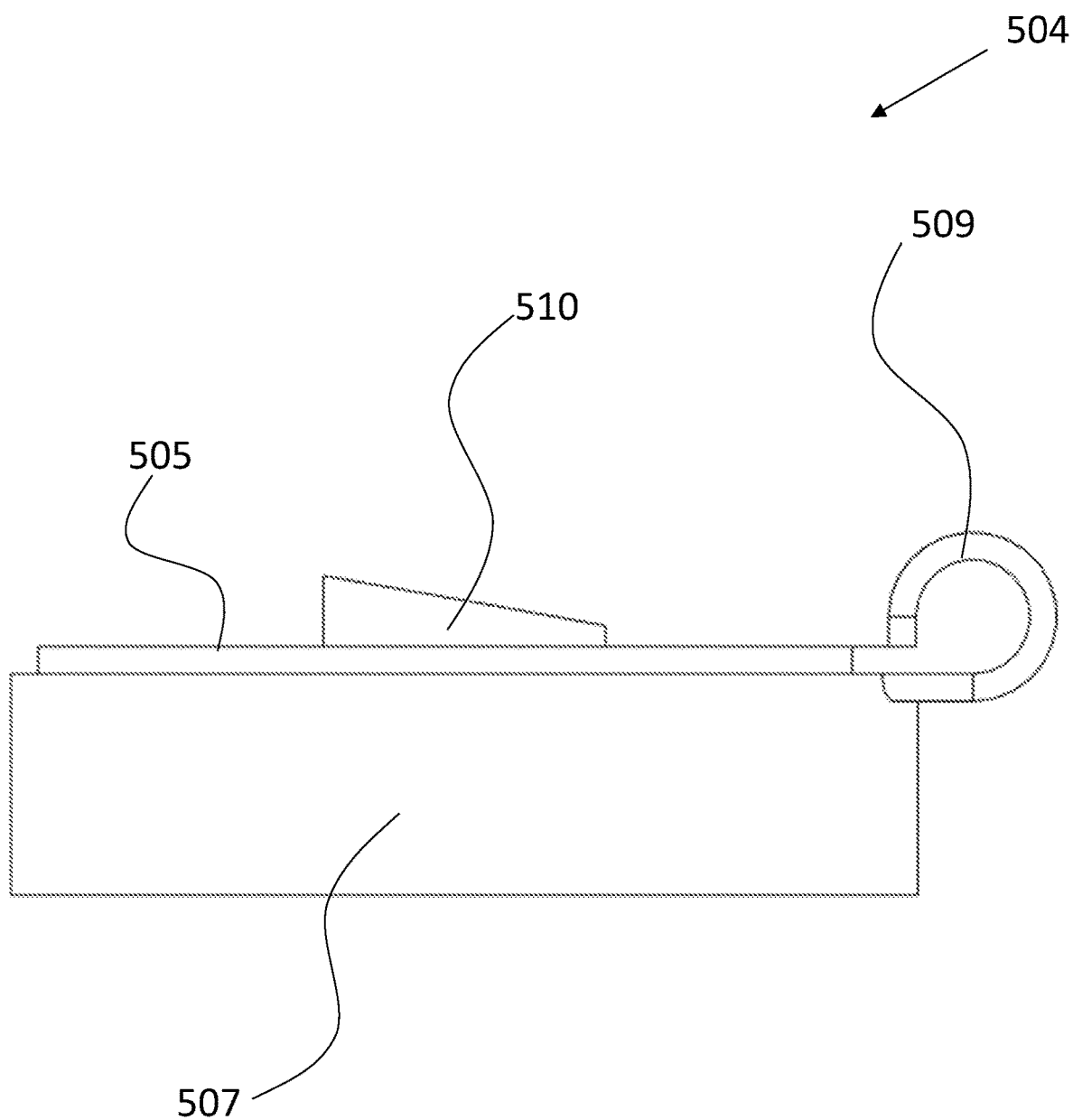
FIG. 28 is a side view of the cover portion of FIG. 27.
Figure 29:
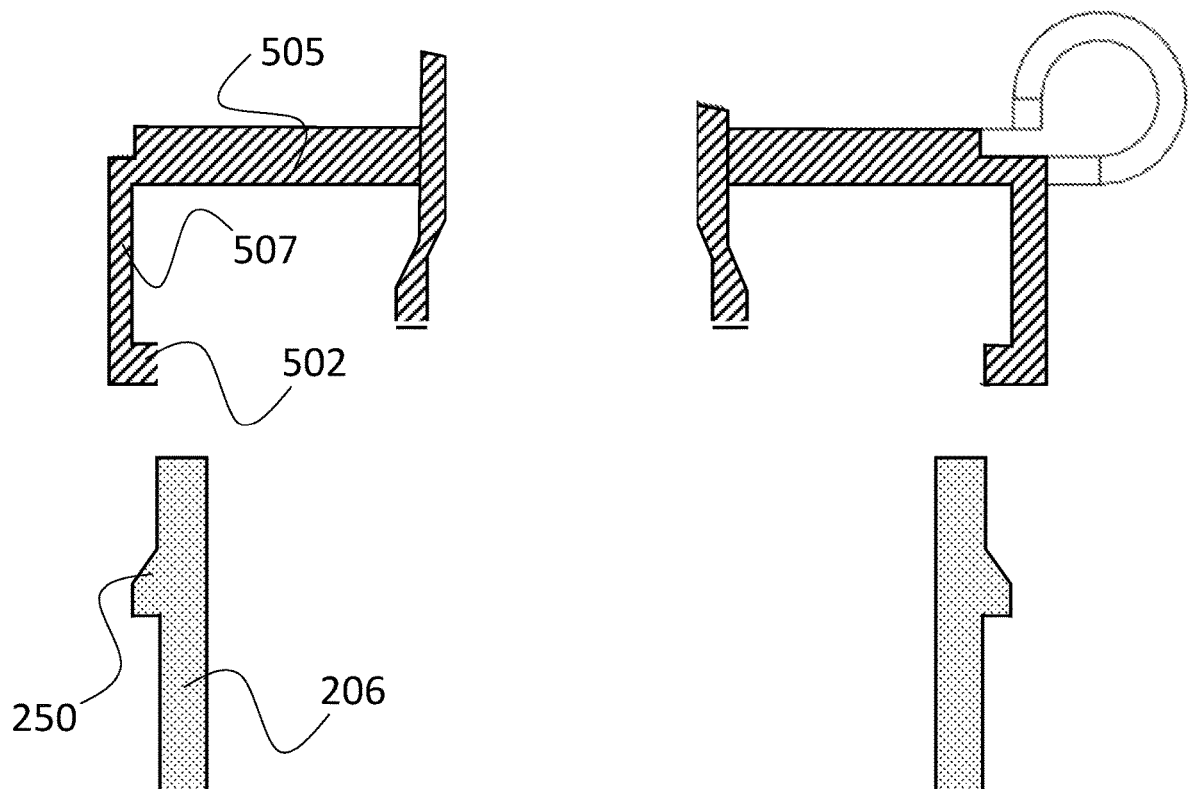
FIGS. 29-32 are side cross sectional views illustrating the snapping cooperation between the cover portion of FIG. 27 and the rimmed second tune of FIG. 25.
Figure 31:
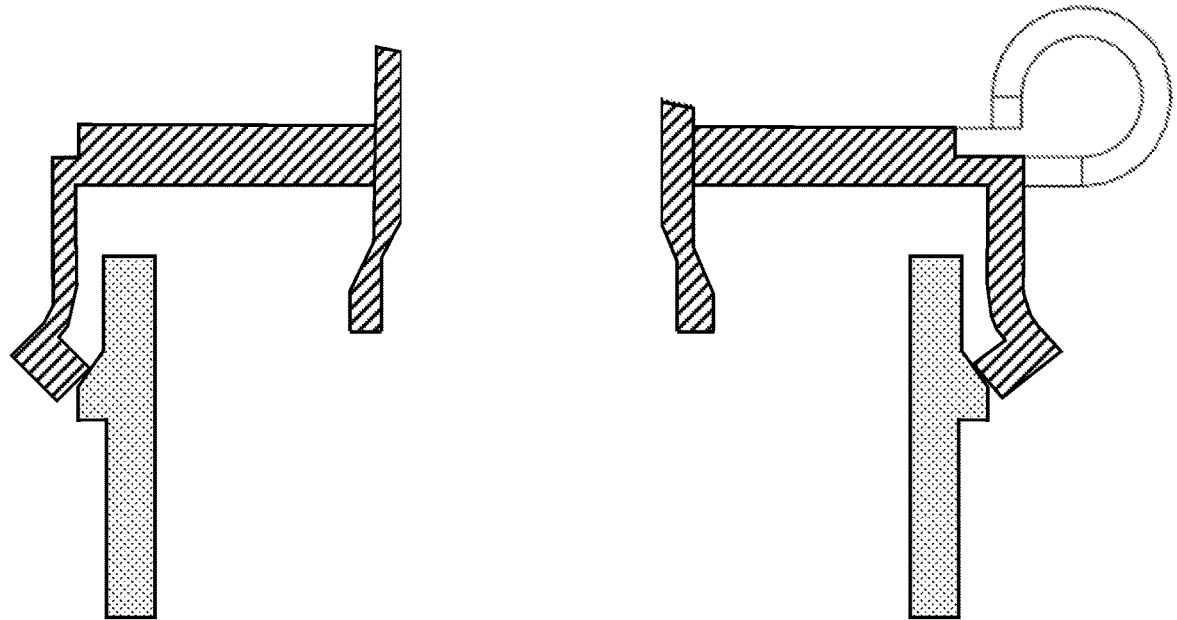
Figure 32:
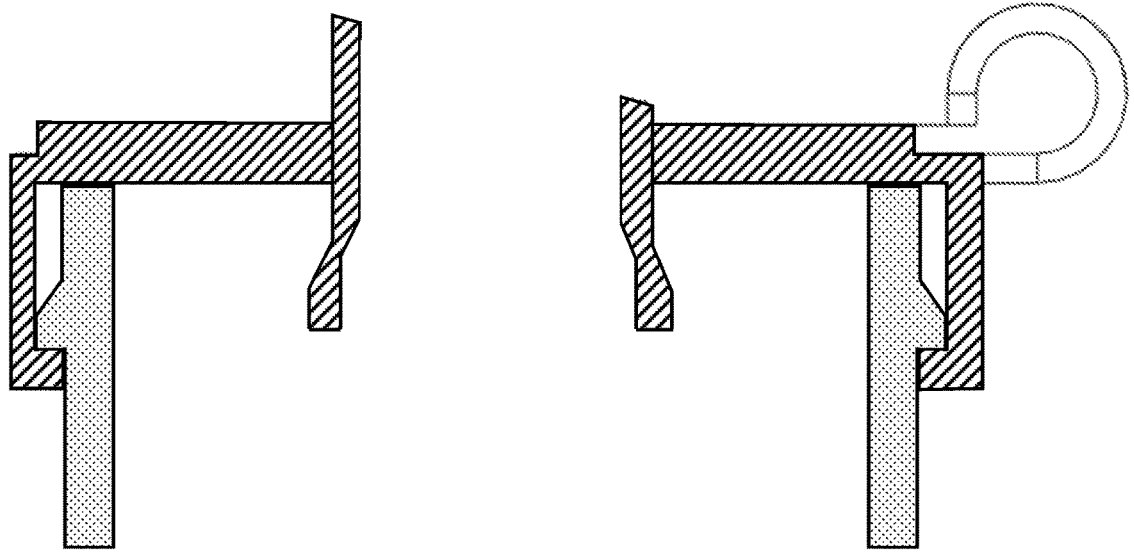
Figure 33:
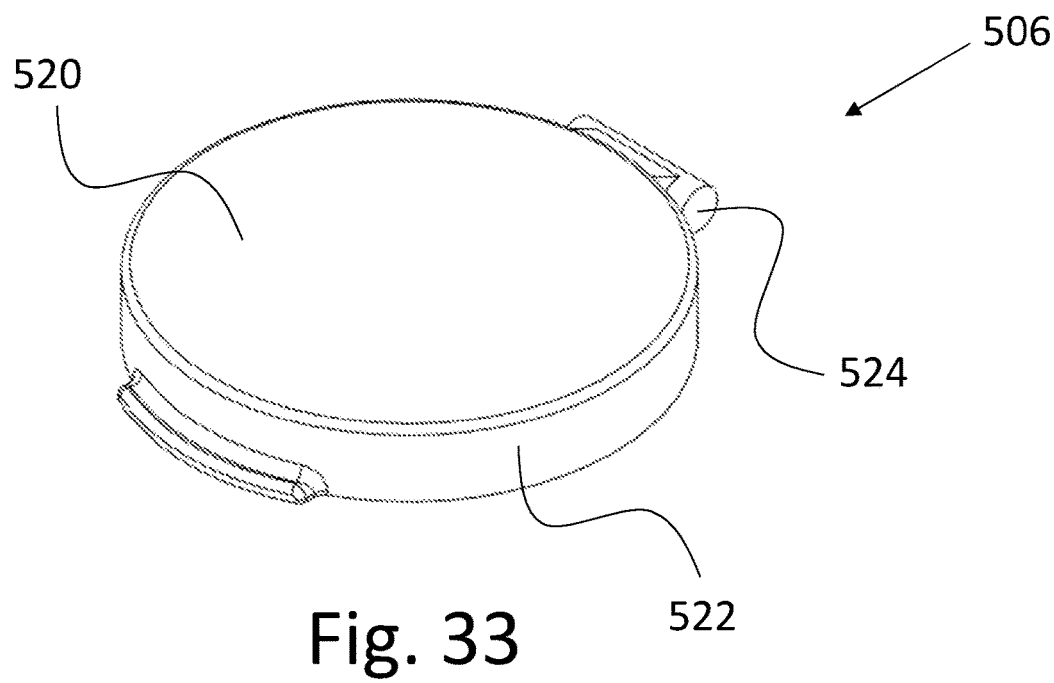
FIG. 33 is perspective view of a lid configured to be associated with the cover portion of FIG. 27, according to some embodiments of the present invention.
Figure 34:
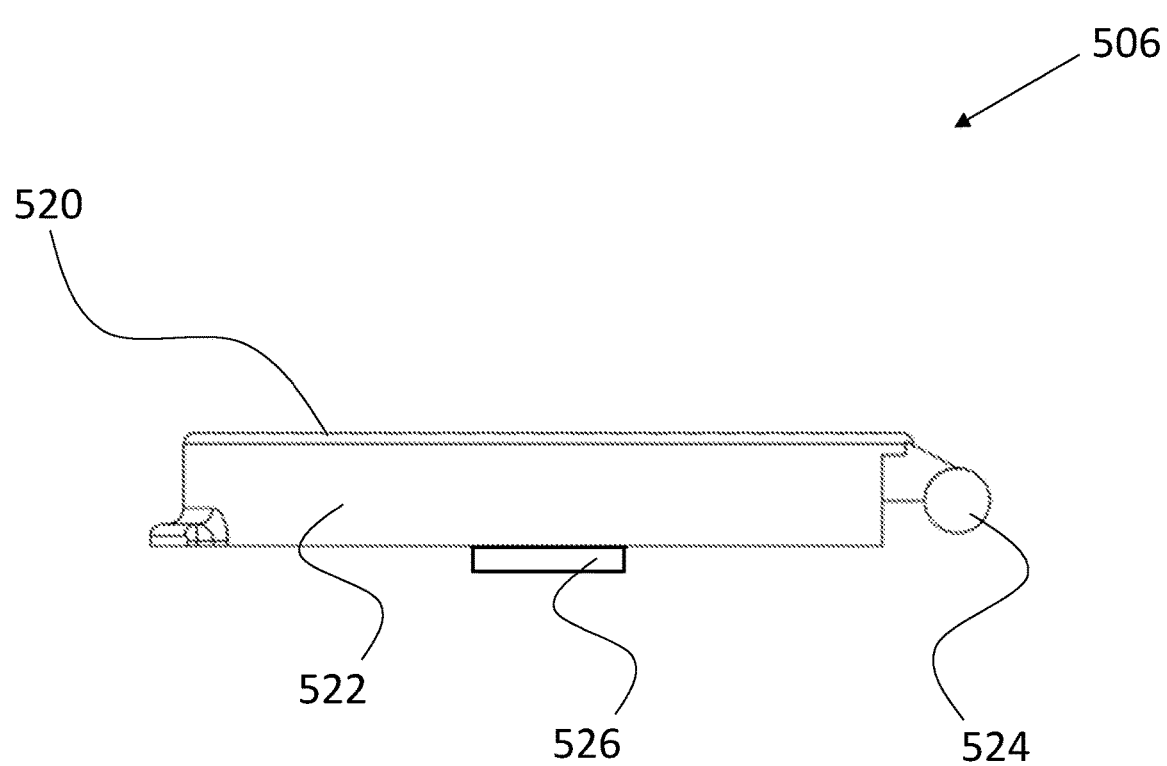
FIG. 34 is a side view of the lid of FIG. 33.
Figure 35:
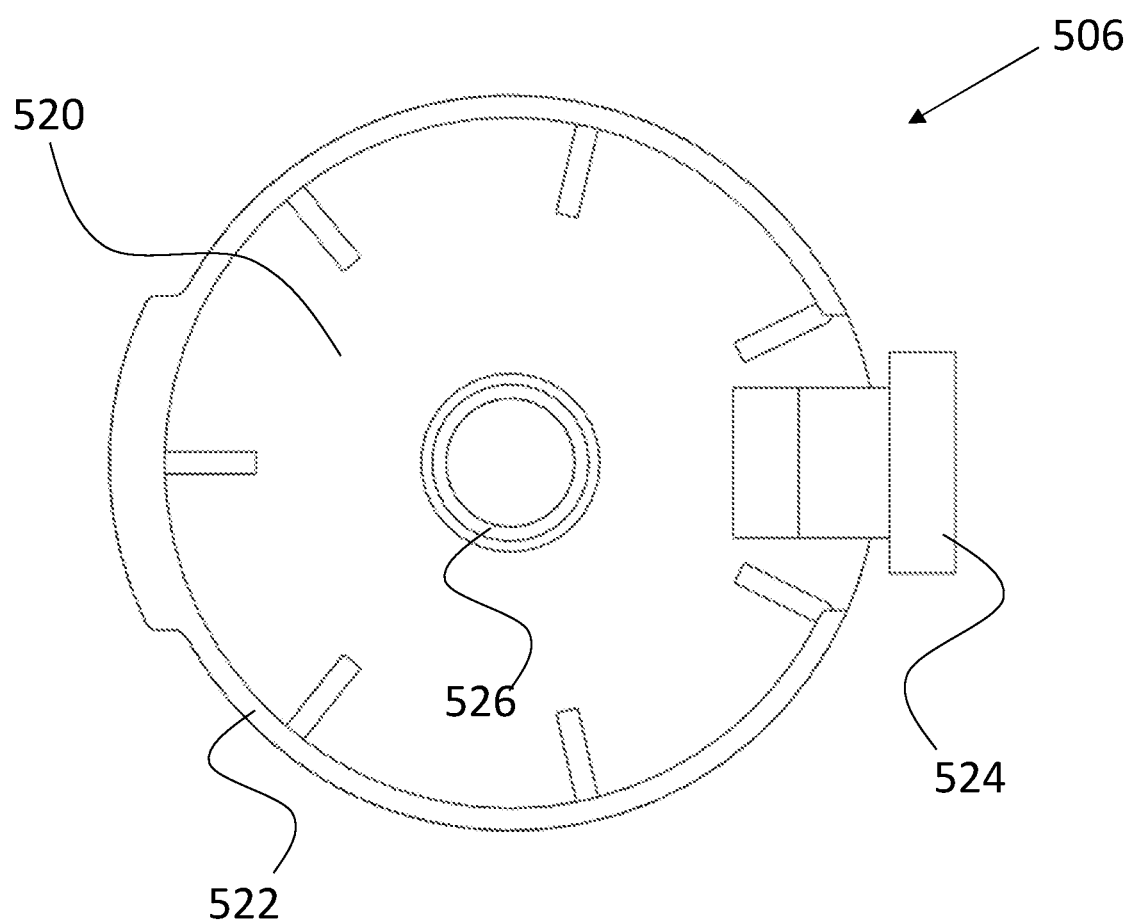
FIG. 35 is a bottom view of the of the lid of FIG. 33.

FIG. 27 is a perspective view of a cover portion of a cap configured for snapping to the rimmed second tube of FIG. 25, according to some embodiments of the present invention. FIG. 28 is a side view of the cover portion of FIG. 27. FIGS. 29-32 are side cross sectional views illustrating the snapping cooperation between the cover portion of FIG. 27 and the rimmed second tune of FIG. 25. FIG. 33 is perspective view of a lid configured to be associated with the cover portion of FIG. 27, according to some embodiments of the present invention. FIG. 34 is a side view of the lid of FIG. 33. FIG. 35 is a bottom view of the of the lid of FIG. 33.

The cap 500 includes cover 504 and a lid 506. The cover 504 is similar to the cover 304 described above, and includes an upper panel 505, an enclosure 507, and a hinge holder 509. The upper panel 505 has a perforation 508, and includes a duct 510. All of the above are similar to the corresponding elements of the cover 304 described above.

Figure 30:
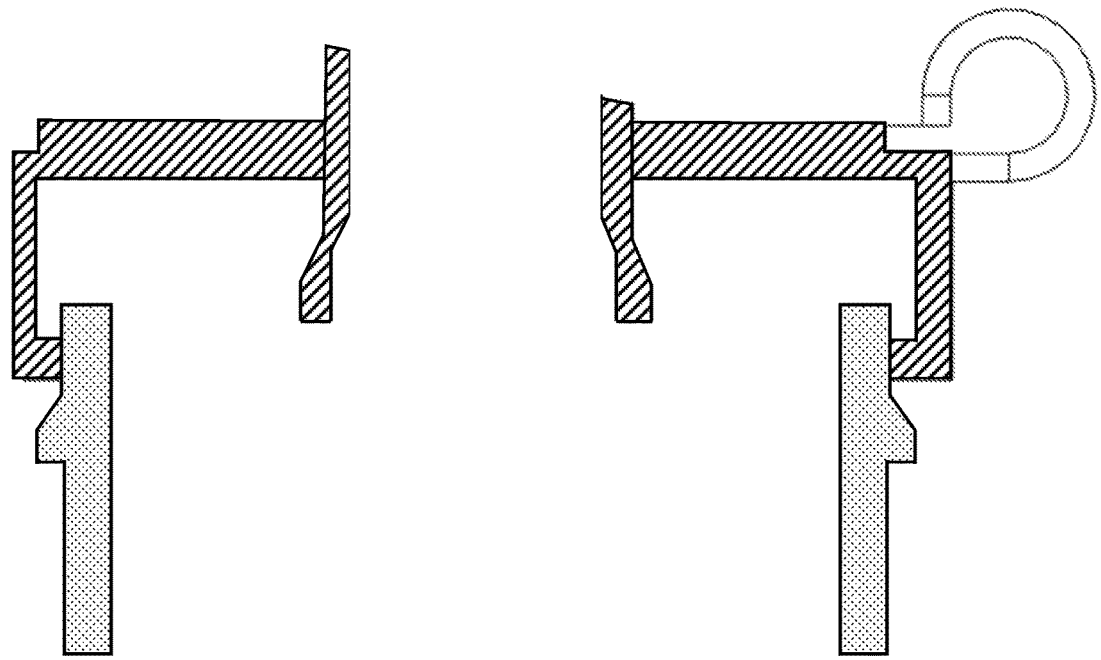

In contrasts to the cover 304, the cover 504 does not include threads. Rather, the enclosure 507 includes a second lip 502 extending radially inward from the inner surface of the enclosure 507. As the cover 504 is lowered onto the second longitudinal wall 206, the second lip 502 contacts the outer surface of the second longitudinal wall (FIG. 30). As the cover is lowered further, the sloping first lip 250 of the second tube 200 presses on the second lip 502 causing a slight expansion of the enclosure 507 (FIG. 31). When the second lip 502 clears the first lip 520, the enclosure elastically snaps back to its rest condition (FIG. 32). The longitudinal length of the enclosure 507 is chosen such that the top surface of the second lip 502 contacts the bottom surface of the first lip 250 when the upper panel 505 contacts the upper edge of the second longitudinal wall 206. In this manner, the tight contact is established between the cover 504 and the second tube 200, preventing liquid escape through the enclosure 507.

Similarly to the lid 306 described above, the lid 506 includes a ceiling 520, a barrier 522, a hinge 524, and a stopper 526. The barrier 522 is a wall that extends downwards from the ceiling 520. The hinge 524 cooperates with the hinge holder 509, such that the lid 506 is hingedly joined to the cover 504. The stopper 526 extends downwards from a middle section of the ceiling 520. When the lid 506 closes the cover 504, the stopper 526 cooperates with the duct 510 to plug the perforation 508 and prevent spillage of the liquid from the second tube, as explained above with reference to the lid 306.

It should be understood that the caps described herein are examples of caps. Any type of cap may be used in conjunction with the second tube 200, as long as the cap can be opened and closed, and when closed provides a hermetic closure that prevents liquid from escaping from the second tube.

What is claimed is:

1. A liquid holding assembly, comprising:
   a first tube, the first tube having a closed first bottom end, an open first top end, and a first longitudinal wall extending between the first bottom end and the first top end, the first longitudinal wall enclosing an inner cavity of the first tube, the first longitudinal wall having a first inner surface and a first outer surface, the first inner surface facing the inner cavity and the first outer surface facing outward from the first tube;
   a second tube configured to be inserted in the first tube, the second tube having a capped second bottom end, a second top end, and a second longitudinal wall extending between the second bottom end and the second top end, the capped second bottom end having a perforation, the second bottom end comprising a holding unit configured to hold a sponge below the second bottom end, and the second bottom end having a perimeter being configured to fit tightly against the first longitudinal wall when inserted into the first tube;
   wherein:
   the second tube is configured to be inserted into the first tube to compress the sponge between the first bottom end and the second bottom end;
   a tight fit between the first longitudinal wall and the perimeter of the second bottom end is configured to prevent passage of liquid in the first tube into the first tube above the second bottom end of the second tube, such that the liquid is forced to travel into the second tube via the perforation in the second bottom end;
   wherein the second tube is sized to removably hold and enclose a test strip; and
   wherein the liquid holding assembly comprises a cap covering the second top end of the second tube, the cap being configured to be opened for insertion of the test strip into the second tube and removal of the test strip from the second tube.

2. The liquid holding assembly of claim 1, wherein the second top end and a portion of a longitudinal length of the second tube is positioned above the first top end of the first tube when the second tube is fully inserted into the first tube.

3. The liquid holding assembly of claim 1, wherein the cap is configured to be removably joined to the second tube.

4. The liquid holding assembly of claim 3, wherein:
   an upper section of the second longitudinal wall comprises first threads;
   the cap comprises second threads configured to cooperate with the first threads;
   the cap is configured to be joined to the second tube by screwing the cap onto the top section of the second longitudinal wall.

5. The liquid holding assembly of claim 1, wherein:
   the cap comprises:
   a cover covering the second top end and having a second perforation;
   a duct extending around and above the second perforation;
   a lid hinged to the cover, the lid being configured to selectively snap onto and away from the cover to close and open the duct.

6. The liquid holding assembly of claim 1, wherein the second tube comprises:
   an upper reservoir located below the second top end; and a channel having a top section located in the upper reservoir and a bottom section extending below the upper reservoir and above the second bottom end, the channel being in fluid communication the upper reservoir and with the perforation at the second bottom end;
wherein the channel is radially narrower than the upper reservoir and the second bottom end.

7. The liquid holding assembly of claim 6, wherein:
the channel is sized to contain a portion of the test strip and to keep the portion of the test strip substantially parallel to a central axis of the second tube.

8. The liquid holding assembly of claim 6, comprising at least two panels extending radially from an outer surface of the bottom section of the channel between the upper reservoir and second bottom end.

9. The liquid holding assembly of claim 1, wherein the first tube comprises a platform below the first bottom end, the platform widening as the platform extends away from the first bottom end.

10. The liquid holding assembly of claim 1, wherein:
the second bottom end comprises a flat platform having a non-zero longitudinal height; and
the second bottom end is radially surrounded by a sealing ring to enhance the tight fit between the first longitudinal wall and the second bottom end.

11. The liquid holding assembly of claim 1, comprising the test strip.

12. The liquid holding assembly of claim 11, wherein:
the liquid is urine; and
the test strip comprises one or more reagent pads configured to react with the urine according to characteristics of the urine, such that a reaction results in a color change of the one or more reagent pads.

13. The liquid holding assembly of claim 1, comprising the sponge.

14. The liquid holding assembly of claim 1, wherein the liquid is urine.

15. A liquid holding assembly, comprising:
a first tube, the first tube having a closed first bottom end, an open first top end, and a first longitudinal wall extending between the first bottom end and the first top end, the first longitudinal wall enclosing an inner cavity of the first tube, the first longitudinal wall having an inner surface and an outer surface, the inner surface facing the inner cavity and the outer surface facing outward from the first tube;
a sponge configured to absorb a liquid;
a test strip configured to react with the liquid upon contact with the liquid;
a second tube configured to removably hold and enclose the test strip and to be inserted in the first tube, the second tube having a capped second bottom end, a second top end, and a second longitudinal wall extending between the second bottom end and the second top end and surrounding the test strip, the capped second bottom end having a perforation, the second bottom end comprising a holding unit configured to hold the sponge below the second bottom end, and the second bottom end having a perimeter being configured to fit tightly against the first longitudinal wall when inserted into the first tube;
a cap covering the second top end of the second tube, the cap being configured to be opened for insertion of the test strip into the second tube and removal of the test strip from the second tube;
wherein:
the second tube is configured to be inserted into the first tube to compress the sponge between the first bottom end and the second bottom end;
the sponge is configured to release the liquid when compressed;
a tight fit between the first longitudinal wall and the perimeter of the second bottom end is configured to prevent passage of the liquid released by the sponge into the first tube above the second bottom end of the second tube, such that the liquid released by the sponge is forced to travel into the second tube via the perforation in the second bottom end and to contact the test strip in the second tube.

16. The liquid holding assembly of claim 15, wherein the cap comprises:
a cover covering the second top end of the second tube having a second perforation;
a duct extending around perforation and upward from the cover;
a lid hinged to the cover, the lid being configured to selectively snap onto and away from the cover to close and open the duct;
wherein the test strip is contained in the second tube such that a bottom portion of the test strip is inside the test strip and configured to contact the liquid released by the sponge, while a top end of the test strip extends out of the second perforation in the duct.

17. The liquid holding assembly of claim 16, wherein the cap is removably joined to the second tube.

18. The liquid holding assembly of claim 15, wherein the liquid is urine and the test strip comprises one or more reagent pads configured to react with the urine according to characteristics of the urine, such that a reaction results in a color change of the one or more reagent pads.

* * * * *